United States Patent [19]

Shimada et al.

[11] Patent Number: 5,210,200
[45] Date of Patent: May 11, 1993

[54] HETEROCYCLIC DYE COMPOUNDS

[75] Inventors: Yasuhiro Shimada; Hisashi Mikoshiba; Hideo Usui, all of Kanagawa, Japan

[73] Assignee: Fuji Photo Film Co., Ltd., Kanagawa, Japan

[21] Appl. No.: 799,192

[22] Filed: Nov. 27, 1991

[30] Foreign Application Priority Data

Nov. 29, 1990 [JP] Japan .................... 2-325583
Nov. 30, 1990 [JP] Japan .................... 2-330774

[51] Int. Cl.$^5$ .......................... C07D 487/04
[52] U.S. Cl. ........................ 548/303.1; 544/370; 544/371; 546/166; 546/271; 548/111; 548/152; 548/360.1; 548/363.1
[58] Field of Search ............... 548/111, 302, 359, 369, 548/192, 303.1; 544/139, 140, 370, 371; 546/166, 271

[56] References Cited

U.S. PATENT DOCUMENTS 5,026,867  6/1991  Yokoyama et al. ............... 548/251

OTHER PUBLICATIONS

Graf et al., Chemical Abstracts, vol. 107 (1987) 39712m.
Abdelhamid, Chemical Abstracts, vol. 99 (1983) 139901g.

*Primary Examiner*—Richard L. Raymond
*Attorney, Agent, or Firm*—Sughrue, Mion, Zinn, Macpeak & Seas

[57] ABSTRACT

A dye compound of a general formula (I):

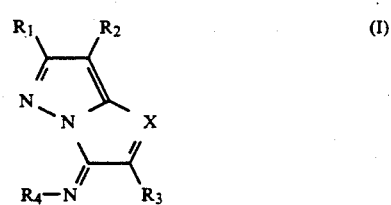

where $R_1$ represents a hydrogen atom, or a substituent; $R_2$ and $R_3$ independently represent a substituent; X represents a nitrogen atom or $—C(R_5)=$; $R_5$ represents a substituent; and $R_4$ represents an aromatic group or an unsaturated heterocyclic group as bonded to the nitrogen atom in the formula via an unsaturated carbon atom, which dye compound is fast to heat and light and is useful for color image formation and as a filter dye; and a thermal transfer dye donating material having a dye donating layer containing a thermal transferring dye on a support, where the thermal transferring dye is represented by:

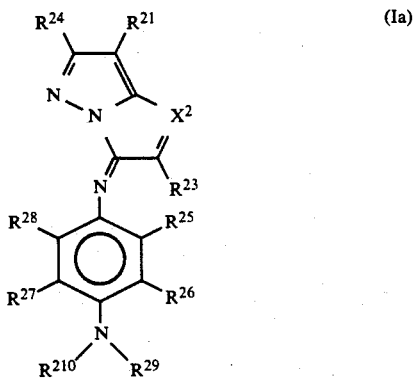

where $X^2$ represents $—N=$, or $—C(R^{22})=$; $R^{21}$, $R^{22}$, $R^{23}$ and $R^{24}$ independently represent a hydrogen atom, or a non-metallic substituent; $R^{25}$, $R^{26}$, $R^{27}$ and $R^{28}$ independently represent a hydrogen atom, or a substituent substitutable on the benzene ring in the formula; $R^{29}$ and $R^{210}$ independently represent a hydrogen atom, an alkyl group, an aryl group, or a heterocyclic group; and $R^{21}$ and $R^{22}$, and/or $R^{22}$ and $R^{23}$, and/or $R^{21}$ and $R^{24}$, and/or $R^{25}$ and $R^{26}$, and/or $R^{26}$ and $R^{29}$, and/or $R^{29}$ and $R^{210}$, and/or $R^{27}$ and $R^{210}$, and/or $R^{27}$ and $R^{28}$ each combine and form a ring.

8 Claims, No Drawings

HETEROCYCLIC DYE COMPOUNDS

FIELD OF THE INVENTION

The present invention relates to novel dye compounds (hereinafter referred to as "dyes") which are usable for formation of color images and as filter dyes.

In addition, it also relates to a thermal transfer dye donating material and, more precisely, to that containing a novel dye which is fast and has a sharp color hue.

BACKGROUND OF THE INVENTION

In general, dyes for formation of images need to satisfy the following requirements.

(1) The color images obtained from them need to be fast to heat and light.

(2) The color images need to have a large molecular extinction coefficient and have a good color hue.

In the past, indoaniline dyes obtained from phenolic or naphtholic compounds and p-phenylenediamines have often been used as cyan dyes for forming color images. However, these indoaniline dyes do not always satisfy requirements (1) and (2) above, and further improvement in such dyes has been desired.

Pyrazolotriazoles of azomethine dyes are described in JP-A-64-48862, JP-A-64-48863 and JP-A-63-145281 as improved. (The term "JP-A" as used herein means an "unexamined published Japanese patent application".) These dyes do provide a sharp color hue having a small side-absorption in a blue light range, but they are not sufficiently fast to light and heat and are therefore are not completely satisfactory.

On the other hand, cyan dyes having excellent properties for use in a thermal transfer system are substantially unknown.

Indoaniline dyes described in JP-A-64-53893, JP-A-64-20194, JP-A-64-24792, JP-A-64-24795, JP-A-63-290793, JP-A-63-308072, JP-A-63-308072, JP-A-1-176593 and JP-A-1-130990 have relatively good properties. However, these dyes still have a broad absorption and color reproduction in forming images is a problem. In addition, images formed of these dyes still do not have sufficient fastness to heat and light. Dyes having a high extinction coefficient are desired since they easily would provide images having a high density. However, the above-mentioned dyes do not have a sufficiently high extinction coefficient.

SUMMARY OF THE INVENTION

One object of the present invention is to provide a novel dye compound which is fast to heat and light, which has a large molecular extinction coefficient and which has an excellent color hue.

Another object of the present invention is to provide a thermal transfer dye donating material which has excellent spectral characteristics, which has excellent transferability and which forms a color image fast to heat and light.

In order to satisfy the objects, the present invention provides a dye compound of the general formula (I):

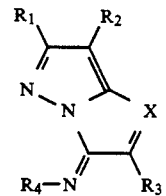

where
- $R_1$ represents a hydrogen atom, or a substituent;
- $R_2$ and $R_3$ independently represent a substituent;
- $X$ represents a nitrogen atom or

- $R_5$ represents a substituent; and
- $R_4$ represents an aromatic group or an unsaturated heterocyclic group bonded to the nitrogen atom in the formula via an unsaturated carbon atom.

Also the present invention provides a thermal transfer dye donating material having a dye donating layer containing a thermal transferring dye on a support, wherein the thermal transfer dye is a dye represented by the following general formula (Ia):

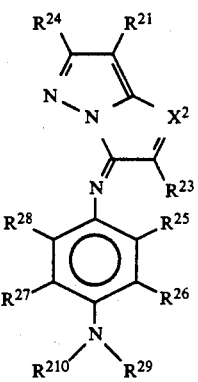

where
$X^2$ represents a nitrogen atom or

- $R^{21}$, $R^{22}$, $R^{23}$ and $R^{24}$ independently represent a hydrogen atom, or a non-metallic substituent;
- $R^{25}$, $R^{26}$, $R^{27}$ and $R^{28}$ independently represent a hydrogen atom, or a substituent on the benzene ring in the formula;
- $R^{29}$ and $R^{210}$ independently represent a hydrogen atom, an alkyl group, an aryl group, or a heterocyclic group; and
- $R^{21}$ and $R^{22}$, and/or $R^{22}$ and $R^{23}$, and/or $R^{21}$ and $R^{24}$, and/or $R^{25}$ and $R^{26}$, and/or $R^{26}$ and $R^{29}$, and/or $R^{29}$ and $R^{210}$, and/or $R^{27}$ and $R^{210}$, and/or $R^{27}$ and $R^{28}$ each may combine with each other and form a ring structure.

BRIEF DESCRIPTION OF THE DRAWINGS

FIG. 1 shows the absorption spectrum of the Dye Compound (10) of the present invention in ethyl acetate compared to that of a conventional phenolic indoaniline Dye (A) in ethyl acetate. The solid line indicates an absorption spectrum of Dye Compound (10); and the dotted line shows that of the comparative Dye (A).

FIG. 2 shows the absorption spectrum of Dye (A-1) of the present invention in an ethyl acetate solution (solid line) and the absorption spectrum of a comparative Dye (a) in an ethyl acetate solution (dotted line).

DETAILED DESCRIPTION OF THE INVENTION

The dye compounds of formula (I) of the present invention are explained in detail below.

In formula (I), $R_1$ represents a hydrogen atom or a substituent. Examples of $R_1$ substituents are a halogen atom, an aliphatic group (preferably having from 1 to 36 carbon atoms), an aromatic group (preferably having from 6 to 36 carbon atoms, such as phenyl, naphthyl), a heterocyclic group (e.g., 3-pyridyl, 2-furyl), an alkoxy group (e.g., methoxy, 2-methoxyethoxy), an aryloxy group (e.g., 2,4-di-tert-amylphenoxy, 2-chlorophenoxy, 4-cyanophenoxy), an alkenyloxy group (e.g., 2-propenyloxy), an amino group (e.g., butylamino, dimethylamino, anilino, N-methylanilino), an aliphatic, aromatic or heterocyclic acyl group (e.g., acetyl, benzoyl), an aliphatic or aromatic oxycarbonyl group (e.g., butoxycarbonyl, phenoxycarbonyl), an aliphatic or aromatic acyloxy group (e.g., acetoxy, benzoyloxy), an aliphatic or aromatic oxysulfonyl group (e.g., butoxysulfonyl), an aliphatic or aromatic sulfonyloxy group (e.g., toluenesulfonyloxy), an acylamino group (e.g., acetylamino), a carbamoyl group (e.g., ethylcarbamoyl, dimethylcarbamoyl), a sulfonamido group (e.g., methanesulfonamido), a sulfamoyl group (e.g., butylsulfamoyl), a sulfamido group (e.g., dipropylsulfamoylamino), an imido group (e.g., succinimido, hydantoinyl), an ureido group (e.g., phenylureido, dimethylureido), an aliphatic, aromatic or heterocyclic sulfonyl group (e.g., methanesulfonyl, benzenesulfonyl), an aliphatic or aromatic thio group (e.g., ethylthio, phenylthio), a hydroxyl group, a cyano group, an carboxyl group or a salt thereof (e.g., sodium salt, potassium salt), a nitro group, and a sulfonic acid group or a salt thereof (e.g., sodium salt, potassium salt).

The "aliphatic group" as referred to herein indicates a linear, branched or cyclic aliphatic hydrocarbon group, for example, saturated or unsaturated alkyl, alkenyl and alkynyl groups. Specific examples of these groups are methyl, ethyl, butyl, dodecyl, octadecyl, eicosenyl, iso-propyl, tert-butyl, tert-octyl, tert-dodecyl, cyclohexyl, cyclopentyl, allyl, vinyl, 2-hexadecenyl, and propargyl groups.

In formula (I), $R_2$ and $R_3$ are independently substituents and they may be same as or different from each other. Preferably, they are substituents having a Hammett's substituent constant $\sigma_p$ value of 0.10 or more, more preferably 0.35 or more.

The Hammett's substituent constant $\sigma_p$ value is described in Hansch, C. Leo et al's reports (e.g., *J. Med. Chem.*, 16, 1207 (1973); ibid., 20, 304 (1977).

Examples of substituents having a Hammett's substituent constant $\sigma_p$ value of 0.10 or more are a substituted alkyl group (e.g., trichloromethyl, trifluoromethyl, heptafluoropropyl, chloromethyl, trifluoromethylthiomethyl, trifluoromethanesulfonylmethyl, perfluorobutyl), a cyano group, an aliphatic, aromatic or heterocyclic acyl group (e.g., formyl, acetyl, benzoyl), a carboxyl group or a salt thereof (e.g., sodium salt, potassium salt), a substituted or unsubstituted carbamoyl group (e.g., carbamoyl, methylcarbamoyl), an alkoxycarbonyl group (e.g., methoxycarbonyl, ethoxycarbonyl, diphenylmethylcarbonyl), a substituted aromatic group (e.g., pentachlorophenyl, pentafluorophenyl), a heterocyclic group (e.g., 2-benzoxazolyl, 2-benzothiazolyl, 1-phenyl-2-benzimidazolyl, 1-tetrazolyl), a nitro group, an azo group (e.g., phenylazo), a substituted amino group (e.g., ditrifluoromethylamino), a substituted alkoxy group (e.g., trifluoromethoxy), an alkylsulfonyloxy group (e.g., methanesulfonyloxy), an acyloxy group (e.g., acetyloxy, benzoyloxy), an arylsulfonyloxy group (e.g., benzenesulfonyloxy), a phosphoryl group (e.g., dimethoxyphosphoryl, diphenylphosphoryl), a sulfamoyl group (e.g., methylsulfamoyl), an aliphatic, aromatic or heterocyclic sulfonyl group (e.g., trifluoromethanesulfonyl, methanesulfonyl, benzenesulfonyl), and a sulfonic acid group or a salt thereof (e.g., sodium salt, potassium salt).

Examples of substituents having a Hammett's substituent constant $\sigma_p$ value of 0.35 or more are a substituted alkyl group (e.g., trifluoromethyl, pentafluoropropyl), a cyano group, an aliphatic, aromatic or heterocyclic acyl group (e.g., acetyl, benzoyl, formyl), a carboxyl group or a salt thereof (e.g., sodium salt, potassium salt), a carbamoyl group (e.g., carbamoyl, methylcarbamoyl), an alkoxycarbonyl group (e.g., methoxycarbonyl, ethoxycarbonyl, diphenylmethylcarbonyl), a substituted aromatic group (e.g., pentafluorophenyl), a heterocyclic group (e.g., 1-tetrazolyl), a nitro group, an azo group (e.g., phenylazo), a substituted amino group (e.g., ditrifluoromethylamino), a substituted alkoxy group (e.g., trifluoromethoxy), an alkylsulfonyloxy group (e.g., methanesulfonyloxy), a phosphoryl group (e.g., dimethoxyphosphoryl, diphenylphosphoryl), a sulfamoyl group (e.g., methylsulfamoyl), an aliphatic, aromatic or heterocyclic sulfonyl group (e.g., trifluoromethanesulfonyl, methanesulfonyl, benzenesulfonyl), and a sulfonic acid group or a salt thereof (e.g., sodium salt, potassium salt).

In formula (I), X represents a nitrogen atom, or $-C(R_5)=$, preferably it is $-C(R_5)=$. $R_5$ is a substituent, more preferably a substituent having a Hammett's substituent constant $\sigma_p$ value of 0.35 or more, especially preferably 0.60 or more. Examples of substituents having a Hammett's substituent constant $\sigma_p$ value of 0.35 or more are those described above for $R_2$ and $R_3$. Examples of substituents having a Hammett's substituent constant $\sigma_p$ value of 0.60 or more are a cyano group, a nitro group, and an aliphatic, aromatic or heterocyclic sulfonyl group (e.g., trifluoromethanesulfonyl, difluoromethanesulfonyl, methanesulfonyl, benzenesulfonyl).

In formula (I), where $R_4$ is an aromatic group, the group preferably has from 6 to 10 carbon atoms, and more preferably $R_4$ is a substituted or unsubstituted phenyl group. Where $R_4$ is a heterocyclic group, the group may be a 5-membered to 7-memberfed unsaturated heterocyclic group having at least one hetero atom selected from nitrogen, oxygen and sulfur atoms. Typical heterocyclic groups are a 2-pyridyl group, a 2-benzothiazolyl group and a 2-pyrrolyl group. $R_4$ is preferably an aromatic group, more preferably a p-disubstituted aminophenyl group.

Preferred examples of the dye compounds of general formula (I) include those wherein $R_2$ is a $CO_2R_{31}$ (wherein $R_{31}$ represents an alkyl group having 1 to 8 carbon atoms) or a $CONHR_{32}$ (wherein $R_{32}$ represents an alkyl group having 1 to 8 carbon atoms or an aryl group having 6 to 18 carbon atoms), $R_3$=$CF_3$ and $R_5$=CN or those wherein $R_2$=CN, $R_3$=$CF_3$ or $C_3F_7$, and $R_5$=CN.

Specific examples of dye compounds of the present invention are described below, but the present invention is not to be construed as being limited to these compounds.

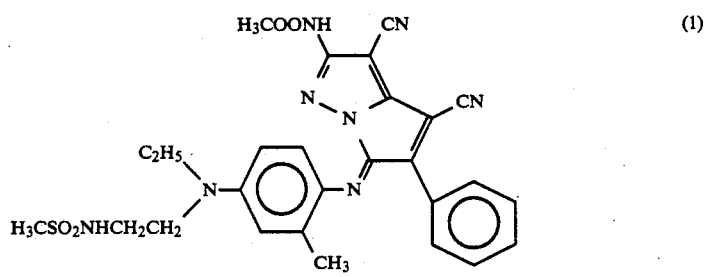

(1)

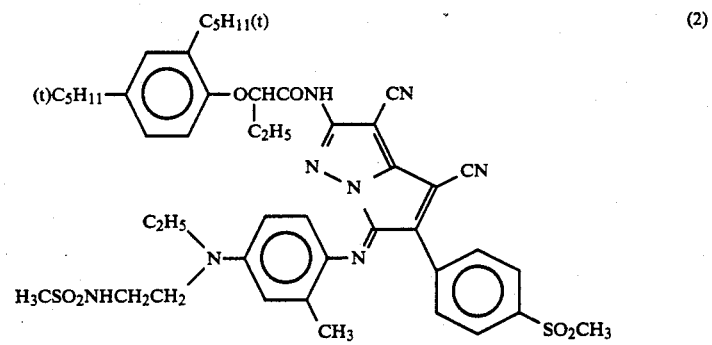

(2)

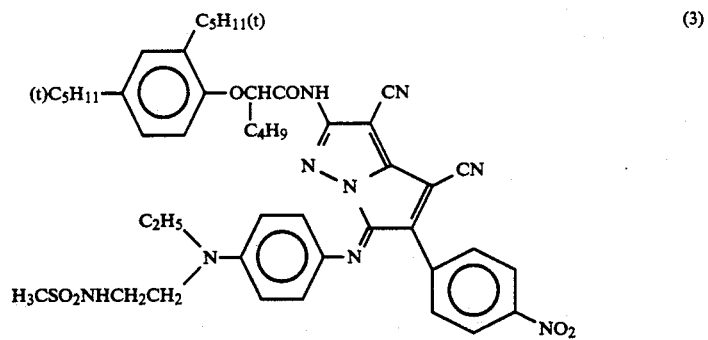

(3)

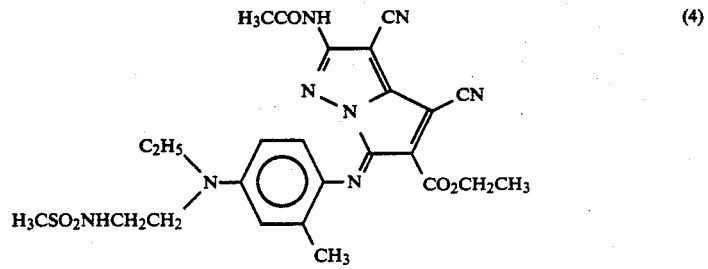

(4)

-continued
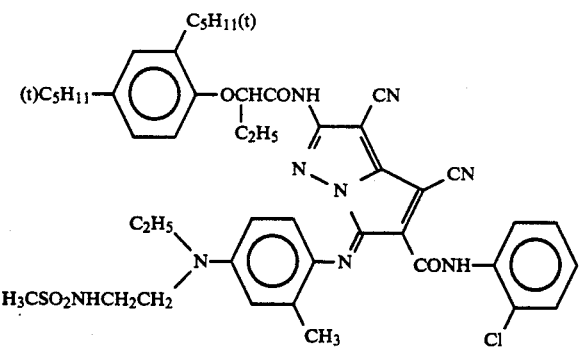
(5)
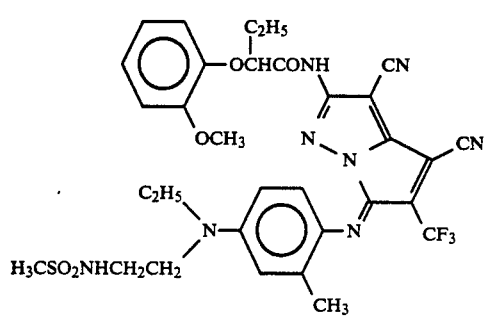
(6)
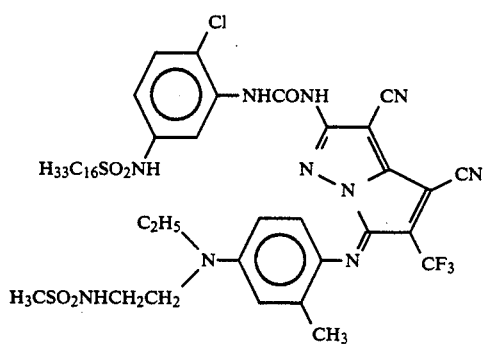
(7)
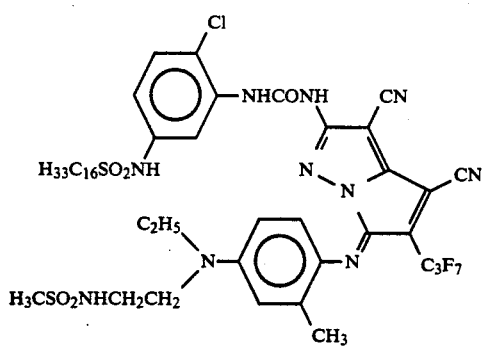
(8)
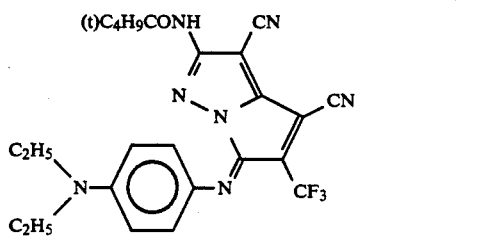
(9)

-continued
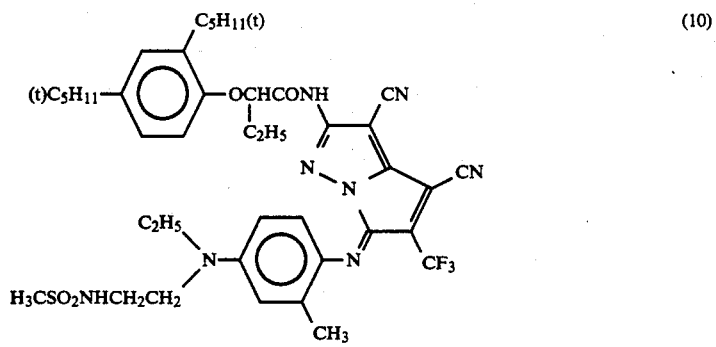
(10)
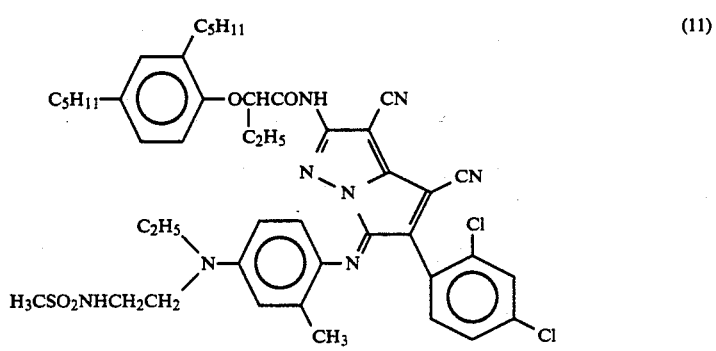
(11)
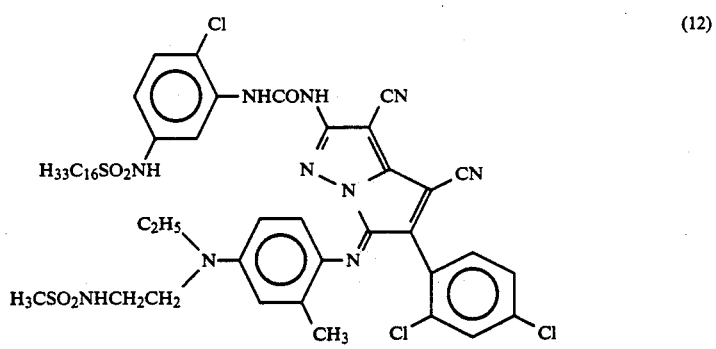
(12)
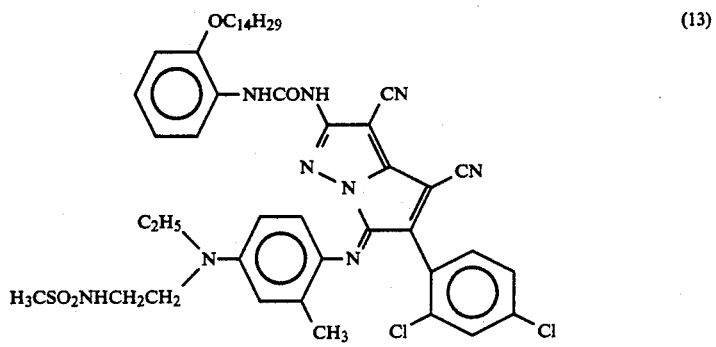
(13)

-continued
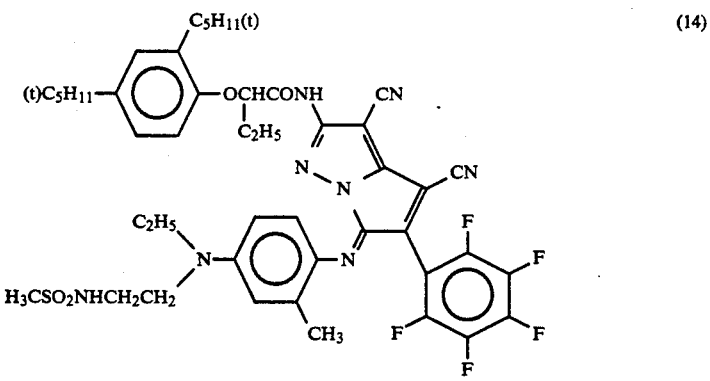
(14)
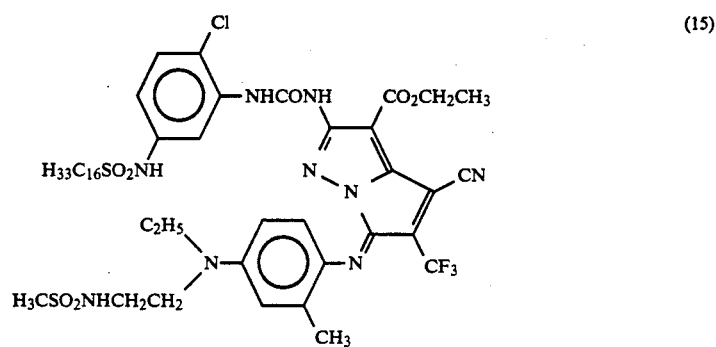
(15)
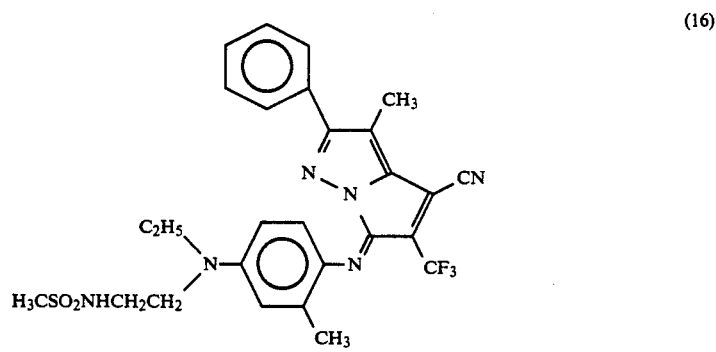
(16)
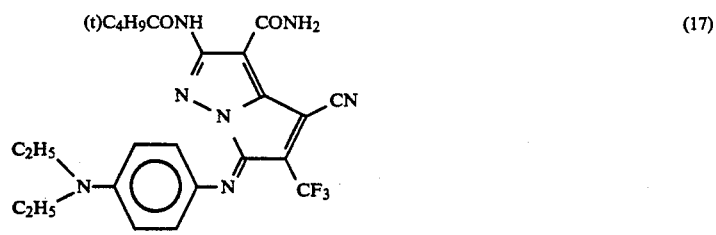
(17)
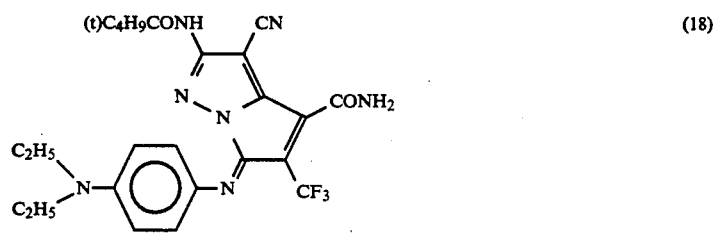
(18)

-continued
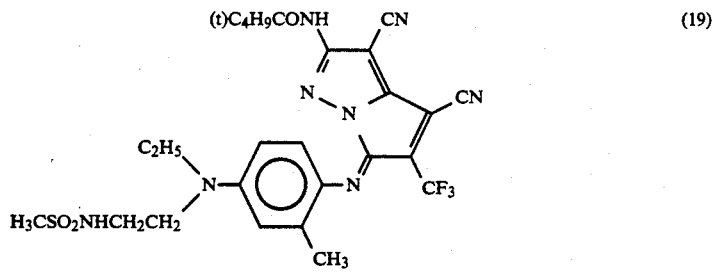
(19)
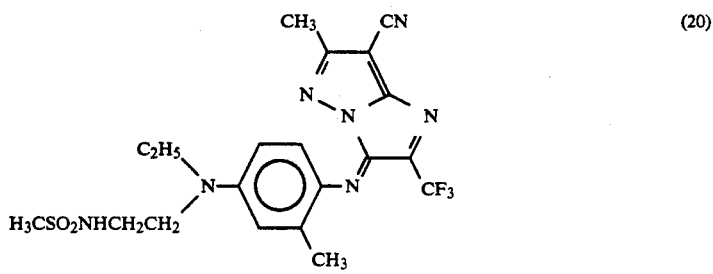
(20)
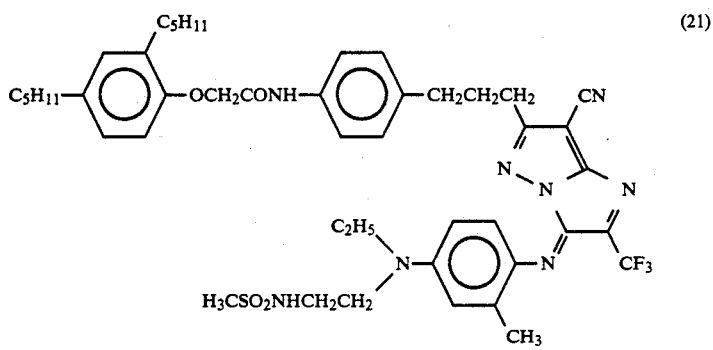
(21)
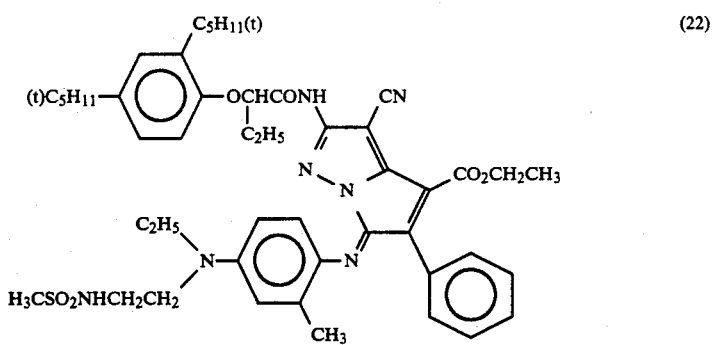
(22)
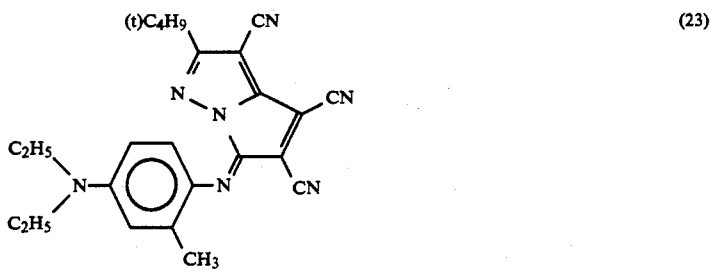
(23)

-continued
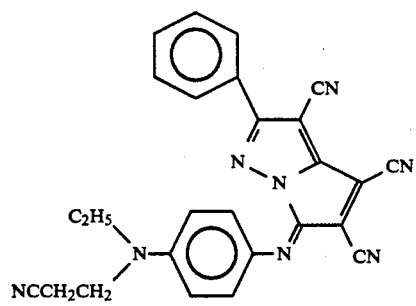
(24)
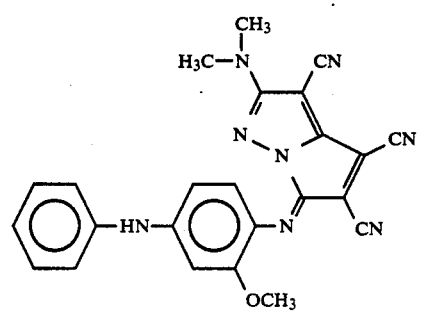
(25)
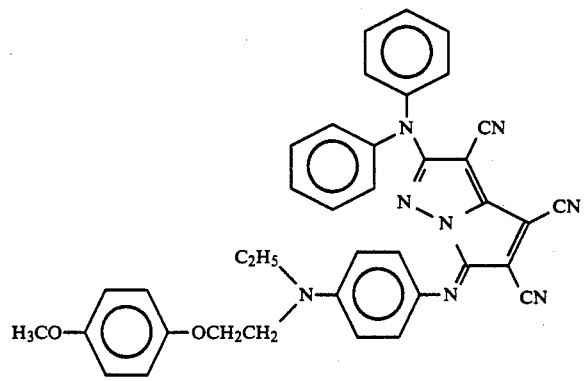
(26)
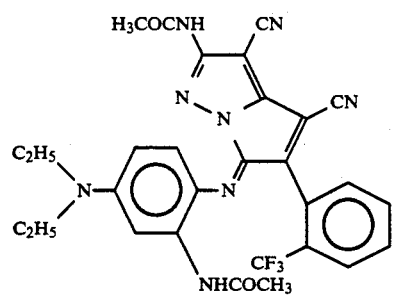
(27)
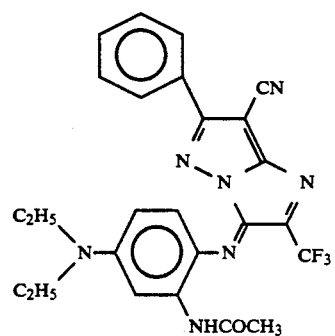
(28)

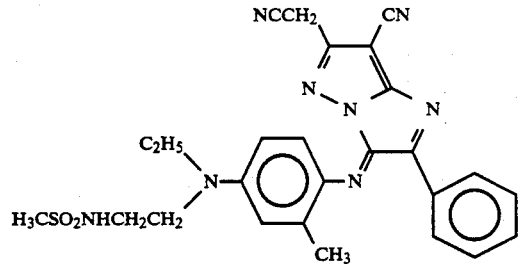
(29)
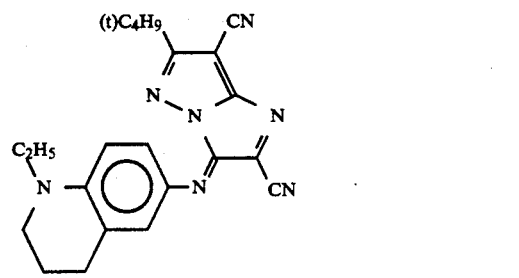
(30)
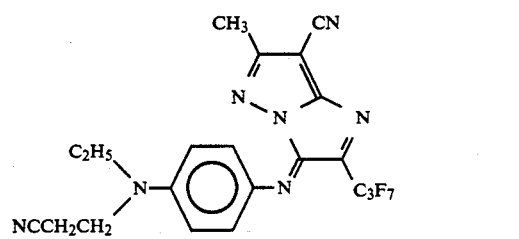
(31)
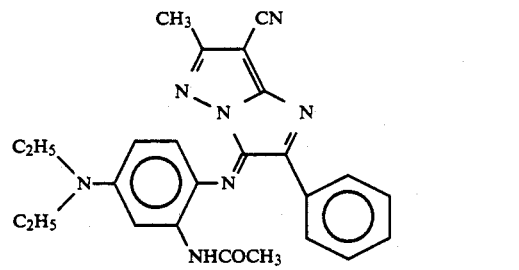
(32)
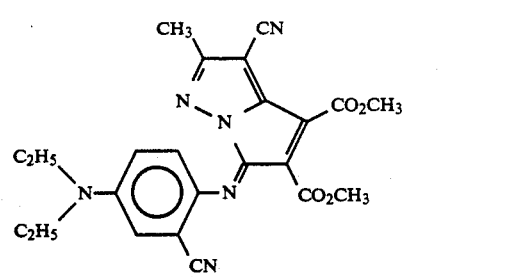
(33)
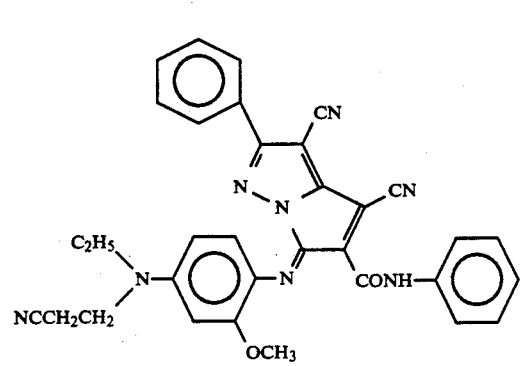
(34)

-continued
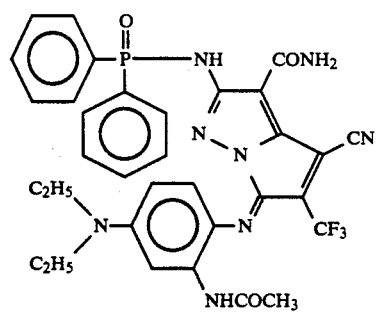
(35)
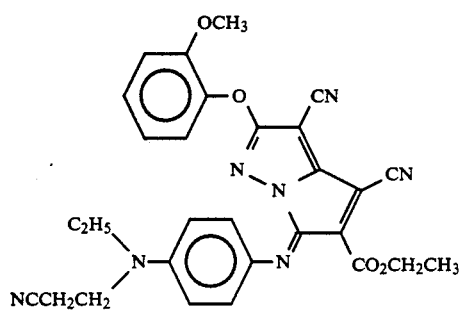
(36)
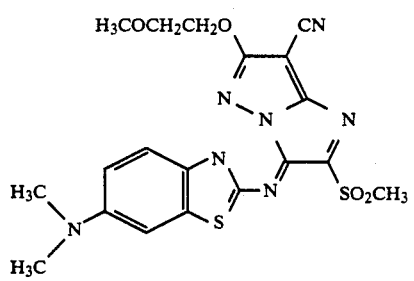
(37)
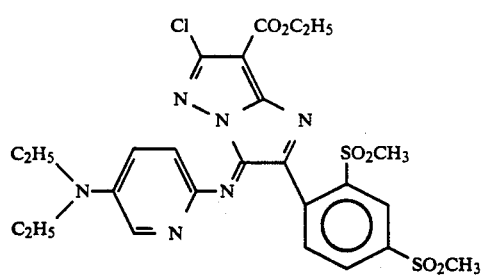
(38)
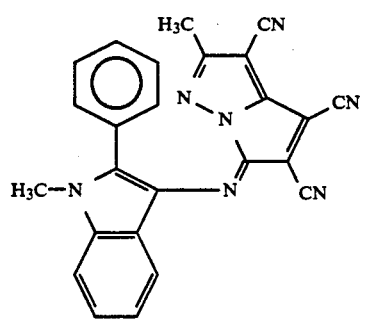
(39)

-continued
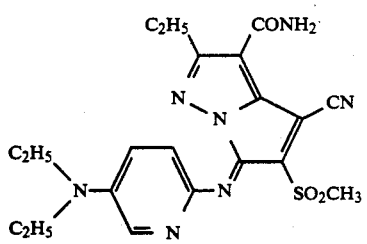 (40)
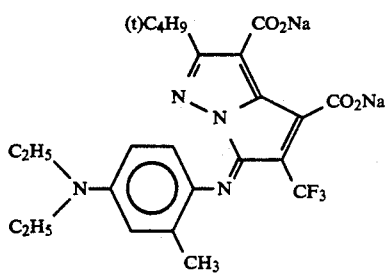 (41)
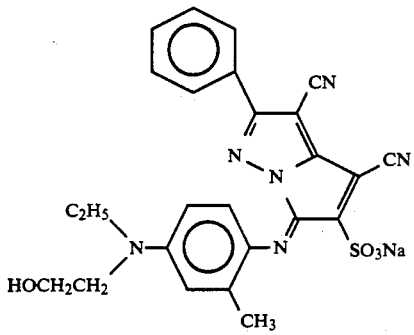 (42)
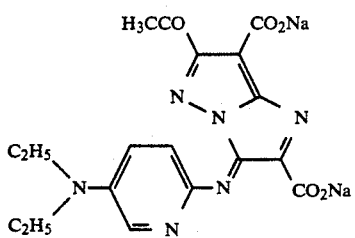 (43)
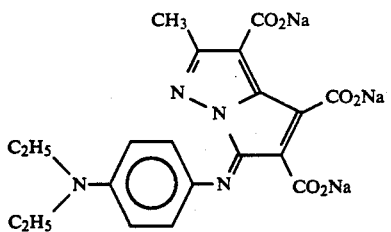 (44)
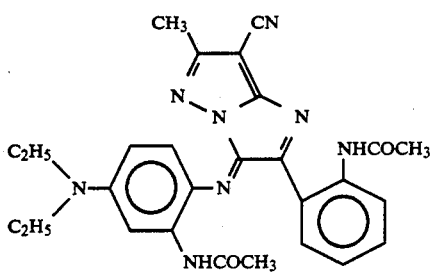 (45)

-continued
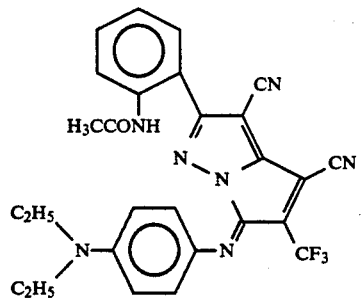
(46)
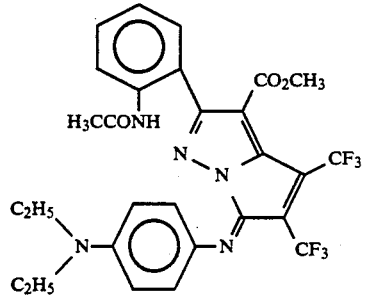
(47)
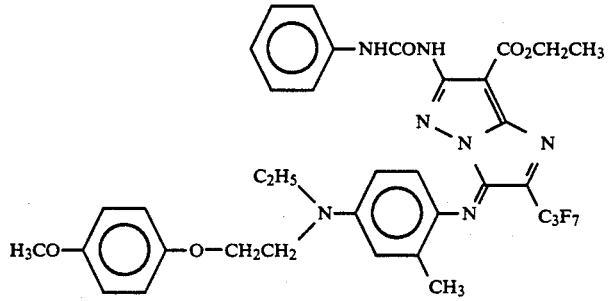
(48)
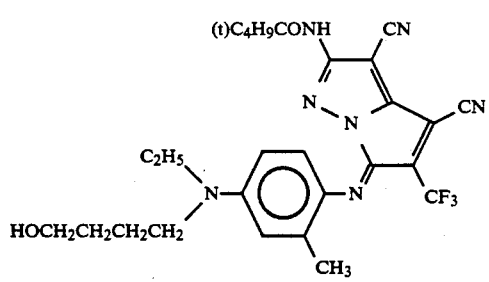
(49)
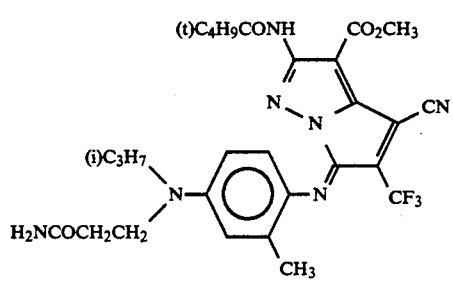
(50)

-continued (51)

[Structure: pyrazolopyridine dye with CONHCH3, CN, CF3, CH3 groups and aniline with (i)C3H7 and H2NCOCH2CH2CH2 substituents]

The dyes of formula (I) can be produced by reacting a coupler of the following general formula (II), which is described in Japanese Patent Application No. 2-121670 or U.S. Pat. No. 4,728,598, and preferably a compound of the following formula (III) or (IV) by oxidation coupling or condensation.

(II)

[Structure of formula II: pyrazole with $R_1$, $R_2$, $R_3$, X, W substituents]

where
  $R_1$, $R_2$, $R_3$ and X have the same meanings as in formula (I); and
  W represents a releasable group which splits off on oxidative coupling.

(III)

[Structure: aniline with $R_{11}$, $R_{12}$ on N, $H_2N$, and $(R_{13})_n$]

(IV)

[Structure: aniline with $R_{11}$, $R_{12}$ on N, ON, and $(R_{13})_n$]

where
  $R_{11}$ and $R_{12}$, which may be the same or different, independently represent a hydrogen atom, or an alkyl group optionally having substituent(s);
  $R_{13}$ represents a hydrogen atom, a halogen atom, a cyano group, or an optionally substituted alkyl, alkoxy or acylamino group; and
  n represents the number of $R_{13}$ substituents and is 1 or 2, and when n is 2, the two $R_{13}$'s may be same or different.

Amines of formula (III) are used preferably in the form of their salts with mineral acids or organic acids, whereupon aerial oxidation may well be prevented and the dissolution speed may be increased.

In formulae (III) and (IV), $R_{11}$ and $R_{12}$ each are preferably a hydrogen atom, an alkyl group, or a substituted alkyl group such as a hydroxyalkyl group, an alkoxyalkyl group, a phenoxyalkyl group, an alkoxyalkoxyalkyl group, a cyanoalkyl group or an alkylsulfonamidoalkyl group.

The alkyl group or the alkyl moiety in the alkoxy or alkoxy-substituted alkyl group in formulae (III) and (IV) may be either a lower alkyl group having from 1 to 4 carbon atoms, such as methyl, ethyl, n-propyl, iso-propyl, n-butyl, iso-butyl, sec-butyl and t-butyl groups, or a higher alkyl group having from 5 to 18 carbon atoms such as n-amyl, dl-2-methyl-1-butyl, iso-amyl, sec-amyl, t-amyl, n-hexyl, methylamyl, 2-ethylbutyl, n-heptyl, 2-heptyl, 3-heptyl, n-octyl, 2-octyl, 2-ethylhexyl, n-dodecyl, n-octadecyl and cyclohexyl groups, and these groups may include linear, branched and cyclic groups. Examples of halogens include chlorine, bromine and iodine.

Primary amines (III) and nitroso compounds (IV) to be used for producing the novel dyes of the present invention are preferably ortho- or para-compounds, more preferably para-compounds. Specific examples of these compounds are:

(1) Compounds having an N-alkyl group, such as;
D1) 4-Amino-N-ethylaniline;
D2) 4-Amino-N,N-diethylaniline;
D3) 4-Nitroso-3-methyl-N,N-diethylaniline;

(2) Compounds having an N-hydroxyalkyl groups, such as;
D4) 4-Amino-N-ethyl-N-(β-hydroxyethyl)aniline;
D5) 4-Nitroso-3-methyl-N-ethyl-N-(β-hydroxyethyl) aniline (3) Compounds having an N-alkoxyalkyl group, such as;
D6) 4-Amino-3-methyl-N-ethyl-(μ-methoxyethyl) aniline;
D7) 4-Amino-3-methyl-N-ethyl-N-methoxybutylaniline;
D8) 4-Nitroso-3-methyl-N-ethyl-N-(μ-ethoxyethyl) aniline;
D9) 4-Amino-3-propyl-N-ethyl-N-(μ-methoxyethyl) aniline;
D10) 4-Amino-3-propyl-N-ethyl-N-(μ-methoxyethyl) aniline;
D11) 4-Amino-3-methoxy-N-ethyl-N-(μ-methoxyethyl) aniline;
D12) 4-Amino-3-methyl-N-ethyl-N-(μ-butoxyethyl) aniline;

(4) compounds having an N-alkoxyalkoxyalkyl group, such as;
D13) 4-Nitroso-3-methyl-N-ethyl-N-(μ-(μ-methoxyethoxy)ethyl)aniline;
D14) 4-Amino-3-methyl-N-ethyl-N-(μ-(μ-ethoxyethoxy) ethyl)aniline;
D15) 4-Nitroso-3-methyl-N-ethyl-N-(μ-(μ-butoxyethyl)ethyl)aniline;

D16) 4-Amino-3-methyl-N-methyl-N-($\mu$-($\mu$-methoxyethoxy)ethyl)aniline

D17) 4-Nitroso-N-ethyl-N-($\mu$-($\mu$-methoxyethoxy)ethyl)aniline;

D18) 4-Amino-N-ethyl-N-($\mu$-($\mu$-ethoxyethoxy)ethyl)aniline; and (5) Compounds having an N-alkylsulfonamidoalkyl group, such as;

D19) 4-Amino-N-ethyl-N-($\mu$-methylsulfonamidoethyl)aniline;

D20) 4-Nitroso-3-methyl-N-ethyl-N-($\mu$-methylsulfonamidoethyl)aniline;

D21) 4-Amino-3-chloro-N-ethyl-N-($\mu$-methylsulfonylamidoethyl)aniline;

D22) 4-Nitroso-N-ethyl-($\mu$-methylsulfonamidoethyl)-3,5-xylidine.

Examples of salts of compounds of formula (III) are hydrohalides such as hydrochlorides, hydrobromides and hydroiodides; inorganic acid salts such as sulfates, nitrates, phosphates and carbonates; organic acid salts such as aliphatic carboxylates (e.g., formates, acetates, propionates), aromatic carboxylates (e.g., benzoates, naphthalene-$\alpha$-carboxylates, naphthalene-$\beta$-carboxylates), aliphatic sulfonates (e.g., methanesulfonates), and aromatic sulfonates (e.g., naphthalene-$\alpha$-sulfonates, naphthalene-$\beta$-sulfonates, p-toluenesulfonates). These are appropriately selected in accordance with the conditions of producing the intended dyes. For instance, if they are used as a photographic color developing agent, they are preferably such that do not adversely influence the photographic properties of the materials to be processed therewith. As a result, in general, the compounds are used in the form of mineral acid salts such as sulfates or aromatic sulfonates such as p-toluenesulfonates.

Dyes of formula (I) where $R_4$ is an unsaturated heterocyclic group can be produced by reacting a coupler of the above-mentioned formula (II) and a compound of the following general formula (V) or (VI) by oxidative coupling or by condensation.

(V) $R_4'$—$NH_2$ 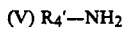

(VI) $R_4'$—$NO$ 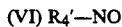

where $R_4'$ is an unsaturated heterocyclic group for $R_4$ in formula (I).

The novel dyes of the present invention are especially useful as photographic cyan dyes, which are obtained, for example, by coupling a coupler of the above-mentioned formula (II) to be used as a cyan coupler in silver halide color photographic material and a developing agent of the above-mentioned formula (III) in the form of an oxidation product thereof oxidized by exposed silver halide.

The novel dyes of the present invention are also useful as filter dyes for photographic materials, disperse dyes or filter dyes for solid television camera tubes or color liquid crystal television sets. In addition, they are also useful as image-forming cyan dyes in a thermal transfer process, ink jet process, color electrophotography and printing process as described in JP-A-58-149048, JP-A-58-18169, JP-A-58-205798 and JP-A-58-219086. Furthermore, the novel dyes of the present invention can be used as thermal transferring dyes in thermal transfer dye donating materials.

The novel dyes of the present invention yield an extremely fast cyan color and they themselves are also extremely fast to light and heat. Additionally, they have an extremely large molecular extinction coefficient.

Thermal transferring dyes of formula (Ia) are explained in detail hereunder.

In formula (Ia), $R^{21}$ to $R^{210}$ represent the above-described groups, and they may optionally be substituted with further substituents.

Precisely, $R^{21}$ represents a hydrogen atom, or a non-metallic substituent. In particular, $R^{21}$ is preferably an electron-attracting group. More precisely, it is preferably a substituent having a Hammett's substituent constant value $\sigma_p$ of 0.10 or more, especially preferably 0.35 or more.

Examples of substituents or atoms having a Hammett's substituent constant $\sigma_p$ value of 0.10 or more are a chlorine atom, a bromine atom, an iodine atom, a substituted alkyl group (e.g., trichloromethyl, trifluoromethyl, chloromethyl, trifluoromethylthiomethyl, trifluoromethanesulfonylmethyl, perfluorobutyl), a cyano group, an aliphatic, aromatic or heterocyclic acyl group (e.g., formyl, acetyl, benzoyl), a carboxyl group, a substituted or unsubstituted carbamoyl group (e.g., carbamoyl, methylcarbamoyl), an alkoxycarbonyl group (e.g., methoxycarbonyl, ethoxycarbonyl, diphenylmethylcarbonyl), a substituted aromatic group (e.g., pentachlorophenyl, pentafluorophenyl), a heterocyclic group (e.g., 2-benzoxazolyl, 2-benzothiazolyl, 1-phenyl-2-benzimidazolyl, 1-tetrazolyl), a nitro group, an azo group (e.g., phenylazo), a substituted amino group (e.g., ditrifluoromethylamino), a substituted alkoxy group (e.g., trifluoromethoxy), an alkylsulfonyloxy group (e.g., methanesulfonyloxy), an acyloxy group (e.g., acetyloxy, benzoyloxy), an arylsulfonyloxy group (e.g., benzenesulfonyloxy), a phosphoryl group (e.g., dimethoxyphosphoryl, diphenylphosphoryl), a sulfamoyl group, and an aliphatic, aromatic or heterocyclic sulfonyl group (e.g., trifluoromethanesulfonyl, methanesulfonyl, benzenesulfonyl).

Examples of substituents having a Hammett's substituent constant $\sigma_p$ value of 0.35 or more are a substituted alkyl group (e.g., trifluoromethyl, pentafluoropropyl), a cyano group, an aliphatic, aromatic or heterocyclic acyl group (e.g., acetyl, benzoyl, formyl), a carboxyl group, a carbamoyl group (e.g., carbamoyl, methylcarbamoyl), an alkoxycarbonyl group (e.g., methoxycarbonyl, ethoxycarbonyl, diphenylmethylcarbonyl), a substituted aromatic group (e.g., pentafluorophenyl), a heterocyclic group (e.g., 1-tetrazolyl), a nitro group, an azo group (e.g., phenylazo), a substituted amino group (e.g., ditrifluoromethylamino), a substituted alkoxy group (e.g., trifluoromethoxy), an alkylsulfonyloxy group (e.g., methanesulfonyloxy), a phosphoryl group (e.g., dimethoxyphosphoryl, diphenylphosphoryl), a sulfamoyl group, and an aliphatic, aromatic or heterocyclic sulfonyl group (e.g., trifluoromethanesulfonyl, methanesulfonyl, benzenesulfonyl).

In formula (Ia), $X^2$ represents —$N$=, or —$C(R^{22})$=. $R^{22}$ is a hydrogen atom or a substituent. Where $R^{22}$ is a substituent, it is preferably an electron-attracting substituent. More preferably, it is a substituent having a Hammett's substituent constant $\sigma_p$ value of 0.35 or more, especially preferably 0.60 or more. Examples of substituents having a Hammett's substituent constant $\sigma_p$ value of 0.35 or more are those described above for $R^{21}$. Examples of substituents having a Hammett's substituent constant $\sigma_p$ value of 0.60 or more are a cyano group, a nitro group, and an aliphatic, aromatic or heterocyclic sulfonyl group (e.g., trifluoromethanesulfonyl, difluoromethanesulfonyl, methanesulfonyl, benzenesulfonyl).

$R^{21}$ and $R^{22}$ each are, preferably, a cyano group, a carbamoyl group, a nitro group, an oxycarbonyl group, or an aliphatic, aromatic or heterocyclic sulfonyl group, and are, especially preferably, a cyano group, or a carbamoyl group.

In formula (Ia), $R^{23}$ and $R^{24}$ are independently a hydrogen atom or a substituent. Examples of substituents, for $R^{23}$ and $R^{24}$ are, for example, a halogen atom, an aliphatic group (preferably having from 1 to 36 carbon atoms), an aromatic group (preferably having from 6 to 36 carbon atoms, e.g., phenyl, naphthyl), a heterocyclic group (e.g. 3-pyridyl, 2-furyl), an alkoxy group (e.g., methoxy, 2-methoxyethoxy), an aryloxy group (e.g., phenoxy, 2-chlorophenoxy, 4-cyanophenoxy), an alkenyloxy group (e.g., 2-propenyloxy), an amino group (e.g., butylamino, dimethylamino, anilino, N-methylanilino), an aliphatic, aromatic or heterocyclic acyl group (e.g., acetyl, benzoyl), an oxycarbonyl group (e.g., butoxycarbonyl, phenoxycarbonyl, methoxycarbonyl), an oxysulfonyl group (e.g., methoxysulfonyl, butoxysulfonyl), an acyloxy group (e.g., acetoxy, benzoyloxy), a sulfonyloxy group (e.g., p-toluenesulfonyloxy), an acylamino group (e.g., acetylamino, ethylbenzoylamino, pivaloylamino), a carbamoyl group (e.g., ethylcarbamoyl, dimethylcarbamoyl), a sulfonylamino group (e.g., methanesulfonylamino, ethanesulfonylamino, benzenesulfonylamino, toluenesulfonylamino), a sulfamoyl group (e.g., methylsulfamoyl, ethylsulfamoyl), a sulfamido group (e.g., dipropylsulfamoylamino), an imido group (e.g., succinimido, hydantoinyl), an ureido group (e.g., phenylureido, dimethylureido), an aliphatic, aromatic or heterocyclic sulfonyl group (e.g., methanesulfonyl, benzenesulfonyl), an aliphatic or aromatic thio group (e.g., ethylthio, phenylthio), a hydroxyl group, a cyano group, and a nitro group.

$R^{23}$ is preferably a substituent having a Hammett's substituent constant $\sigma_p$ value of 0.10 or more, especially preferably 0.35 or more.

The "aliphatic group" as referred to herein is a linear, branched or cyclic aliphatic hydrocarbon group, for example, saturated or unsaturated alkyl, alkenyl and alkynyl groups. Specific examples of such groups are methyl, ethyl, butyl, iso-propyl, tert-butyl, trifluoromethyl, cyclohexyl, cyclopentyl, allyl, vinyl, and propargyl groups.

$R^{25}$, $R^{26}$, $R^{27}$ and $R^{28}$ are independently a hydrogen atom or a substituent on the benzene ring in formula (Ia). Preferably, they each are a hydrogen atom, an alkyl group, an alkoxy group, an aryloxy group, a halogen atom, an acylamino group, an alkoxycarbonyl group, a cyano group, an alkoxycarbonylamino group, an aryloxycarbonylamino group, an aminocarbonylamino group, a sulfonylamino group, an carbamoyl group, a sulfamoyl group, an aryl group, an alkylthio group, an arylthio group, a sulfonyl group, an acyl group or an amino group.

Specific examples of $R^{25}$, $R^{26}$, $R^{27}$ and $R^{28}$ include a hydrogen atom, a substituted or unsubstituted alkyl group (having from 1 to 12 carbon atoms, e.g., methyl, ethyl, isopropyl, butyl, methoxyethyl, cyclohexyl, phenethyl), a substituted or unsubstituted alkoxy group (having from 1 to 12 carbon atoms, e.g., methoxy, ethoxy, isopropoxy, methoxyethoxy), a substituted or unsubstituted aryloxy group (having from 6 to 12 carbon atoms, e.g., phenoxy, p-methoxyphenoxy, p-chlorophenoxy, p-methylphenoxy) a halogen atom (e.g., fluorine, chlorine, bromine), an acylamino group (for example, a substituted or unsubstituted alkylcarbonylamino having from 1 to 10 carbon atoms, e.g., formylamino, acetylamino, propionylamino, isobutylamino, hexahydrobenzoylamino, pivaloylamino, trifluoroacetylamino, heptafluorobutyrylamino, chloropropionylamino, cyanoacetylamino, phenoxyacetylamino; a substituted or unsubstituted vinylcarbonylamino group having form 3 to 10 carbon atoms, e.g., acryloylamino, methacryloylamino, crotonoylamino; a substituted or unsubstituted arylcarbonylamino group having from 7 to 15 carbon atoms, e.g., benzoylamino, p-toluylamino, pentafluorobenzoylamino, o-fluorobenzoylamino, m-methoxybenzoylamino, p-trifluoromethylbenzoylamino, 2,4-dichlorobenzoylamino, p-methoxycarbonylbenzoylamino, 1-naphthylamino; or a substituted or unsubstituted heterylcarbonylamino group having from 5 to 13 carbon atoms, e.g., piconoylamino, nicotinoylamino, pyrrole-2-carbonylamino, thiophene-2-carbonylamino, furoylamino, piperidine-4-carbonylamino), a cyano group, a substituted or unsubstituted alkoxycarbonyl group (having from 2 to 10 carbon atoms, e.g., methoxycarbonyl, ethoxycarbonyl), a substituted or unsubstituted alkoxycarbonylamino group (having from 2 to 10 carbon atoms, e.g., methoxycarbonylamino, ethoxycarbonylamino, isopropoxycarbonylamino, methoxyethoxycarbonylamino, N-methylmethoxycarbonylamino, t-butoxycarbonylamino, hexyloxycarbonylamino), a substituted or unsubstituted aryloxycarbonylamino group (having from 7 to 15 carbon atoms, e.g., phenoxycarbonylamino, orthochlorophenoxycarbonylamino), a substituted or unsubstituted aminocarbonyl group (having from 1 to 10 carbon atoms, e.g., methylaminocarbonylamino, dimethylaminocarbonylamino, butylaminocarbonylamino), a sulfonylamino group (having from 1 to 10 carbon atoms, e.g., methanesulfonylamino, ethanesulfonylamino, N-methylmethanesulfonylamino, benzenesulfonylamino), a carbamoyl group (for example, a substituted or unsubstituted alkylcarbamoyl group having from 1 to 12 carbon atoms, e.g., methylcarbamoyl, dimethylcarbamoyl, butylcarbamoyl, isopropylcarbamoyl, t-butylcarbamoyl, cyclopentylcarbamoyl, cyclohexylcarbamoyl, allylcarbamoyl, methoxyethylcarbamoyl, chloroethylcarbamoyl, cyanoethylcarbamoyl, ethylcyanoethylcarbamoyl, benzylcarbamoyl, ethoxycarbonylmethylcarbamoyl, furfurylcarbamoyl, tetrahydrofurfurylcarbamoyl, phenoxymethylcarbamoyl; a substituted or unsubstituted arylcarbamoyl group having from 7 to 15 carbon atoms, e.g., phenylcarbamoyl, p-toluylcarbamoyl, m-methoxyphenylcarbamoyl, 4,5-dichlorophenylcarbamoyl, p-cyanophenylcarbamoyl, p-acetylaminophenylcarbamoyl, p-methoxycarbonylphenylcarbamoyl, m-trifluoromethylphenylcarbamoyl, o-fluorophenylcarbamoyl, 1-naphthylcarbamoyl; or a substituted or unsubstituted heterylcarbamoyl group having from 4 to 12 carbon atoms, e.g., 2-pyridylcarbamoyl, 3-pyridylcarbamoyl, 4-pyridylcarbamoyl, 2-thiazolylcarbamoyl, 2-benzothiaozlylcarbamoyl, 2-benzimidazolylcarbamoyl, 2-(4-mehtyl)pyridylcarbamoyl, 2-(5-methyl)-1,3,4-thiadiazolylcarbamoyl), a sulfamoyl group (having from 0 to 12 carbon atoms, e.g., methylsulfamoyl, dimethylsulfamoyl, butylsulfamoyl, phenylsulfamoyl), a substituted or unsubstituted aryl group (e.g., phenyl, p-tolyl, p-methoxyphenyl, p-chlorophenyl), a substituted or unsubstituted alkylthio group (e.g., methylthio, butylthio), a substituted or unsubstituted arylthio group (e.g., phenylthio, p-tolylthio), a sulfonyl group (e.g., methanesulfonyl, butanesulfonyl, benzenesulfonyl), an acyl group (e.g., acetyl, butyroyl), and an amino group (e.g., methylamino, dimethylamino, anilino).

$R^{25}$ is preferably a hydrogen atom, an alkyl group having from 1 to 4 carbon atoms, an alkoxy group having from 1 to 3 carbon atoms, a halogen atom (e.g., fluorine, chlorine, bromine), an acylamino group having form 1 to 4 carbon atoms, a sulfonylamino group having from 1 to 4 carbon atoms, an aminocarbonylamino group having from 1 to 4 carbon atoms, or an alkoxycarbonylamino group having from 2 to 5 carbon atoms.

$R^{26}$, $R^{27}$ and $R^{28}$ are preferably hydrogen atoms.

$R^{29}$ and $R^{210}$ are independently a hydrogen atom, a substituted or unsubstituted alkyl group (having from 1 to 12 carbon atoms, e.g., methyl, ethyl, isopropyl, butyl, cyclopentyl, cyclohexyl, 2-methoxyethyl, 2-chloroethyl, 2-hydroxyethyl, 2-cyanoethyl, cyanomethyl, 2-methylsulfamoylethyl, 2-methanesulfonylaminoethyl, 2-methoxycarbonylethyl, 2-acetoxyethyl, methoxycarbonylmethyl, benzyl, allyl), a substituted or unsubstituted aryl group (having from 6 to 12 carbon atoms, e.g., phenyl, p-tolyl, m-chlorophenyl), or a substituted or unsubstituted heterocyclic group (having from 4 to 12 carbon atoms, e.g.,

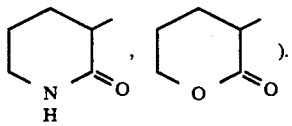

Especially preferably, $R^{29}$ and $R^{210}$ each are an alkyl group having from 1 to 6 carbon atoms.

$R^{29}$ and $R^{210}$ may combine with each other to form a ring, which preferably includes, for example,

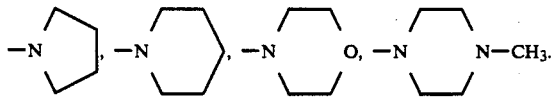

$R^{26}$ and $R^{29}$, or $R^{27}$ and $R^{210}$ may also combine with each other to form a ring, which preferably includes, for example,

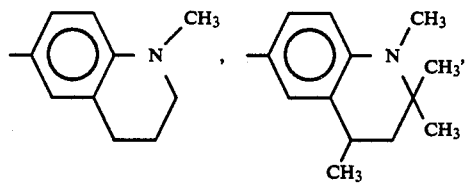

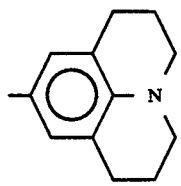

The dyes of the present invention may contain an atomic group having an anti-fading effect in the dye molecule. Introduction of such an anti-fading atomic group into the dyes is especially preferred when the dyes are to form color images with high fastness.

Such an anti-fading atomic group may be bonded to any of $R^{21}$, $R^{22}$, $R^{23}$, $R^{24}$, $R^{25}$, $R^{26}$, $R^{27}$, $R^{28}$, $R^{29}$ and $R^{210}$ in the dyes.

Preferred examples of the dyes of general formula (Ia) include those wherein $R_{21}$ is a $CO_2R_{41}$ (wherein $R_{41}$ represents an alkyl group having 1 to 8 carbon atoms) or a $CONHR_{42}$ (wherein $R_{42}$ represents an alkyl group having 1 to 8 carbon atoms or an aryl group having 6 to 18 carbon atoms), $R_{23}=CF_3$ and $R_{22}=CN$ and those wherein $R_{21}=CN$, $R_{23}=CF_3$ or $C_3F_7$, and $R_{22}=CN$.

Examples of an anti-fading atomic group which may be used in the dyes of the present invention are described in Japanese Patent Application No. 1-27078 are usable.

Specific examples of anti-fading atomic groups usable in the present invention are mentioned below, which, however, are not limitative.

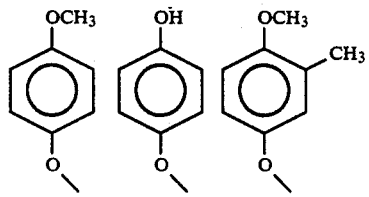

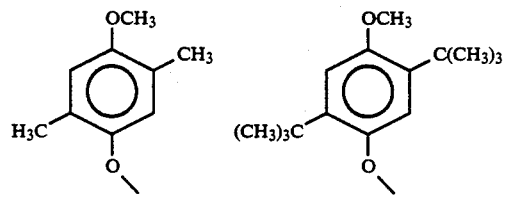

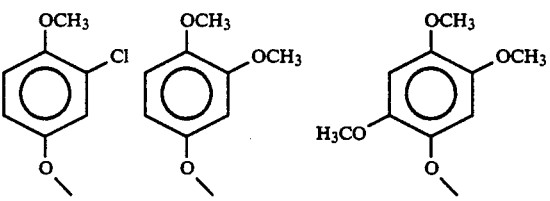

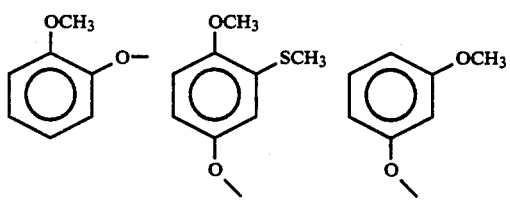

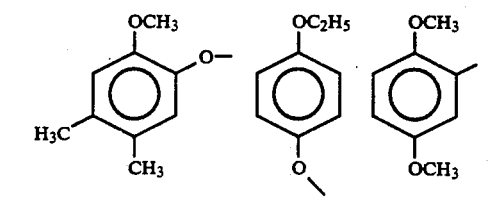

33
-continued
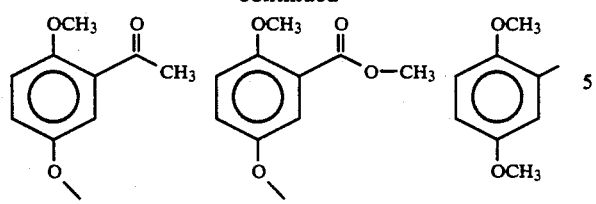
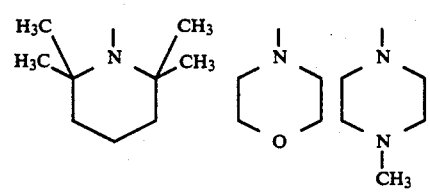
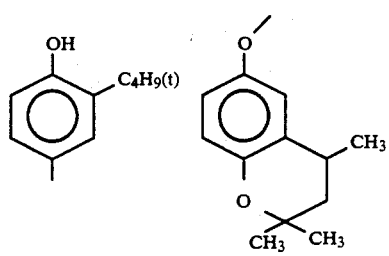
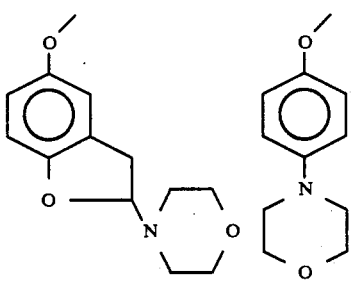
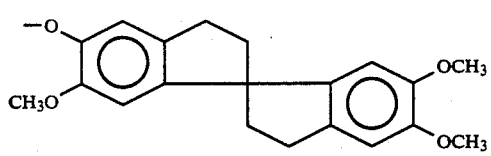
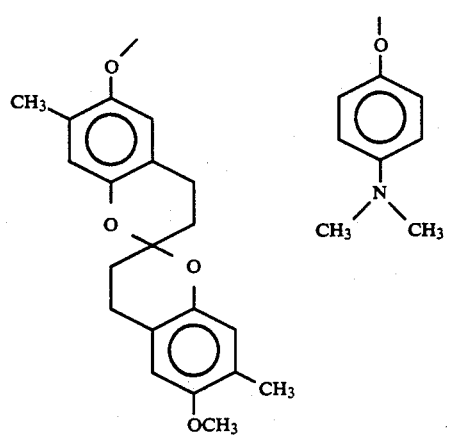
34
-continued
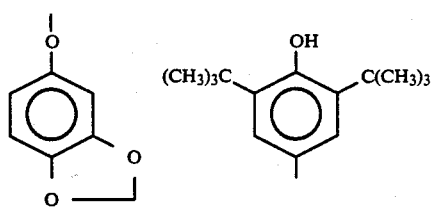
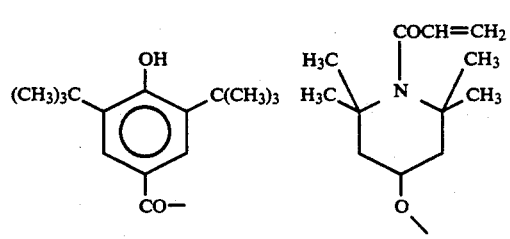
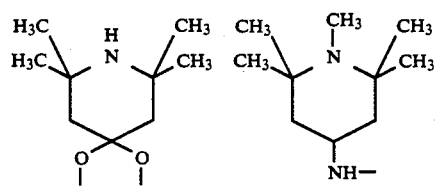
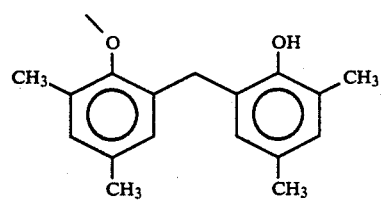
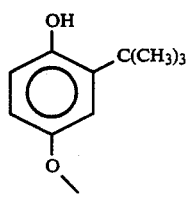
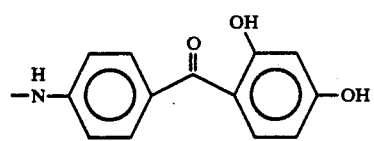
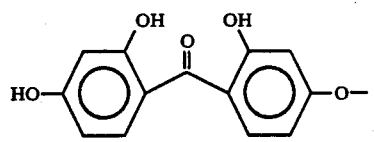
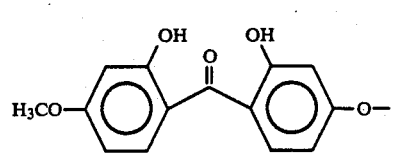

-continued
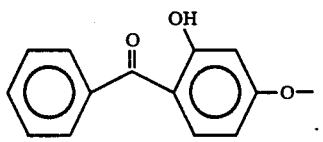
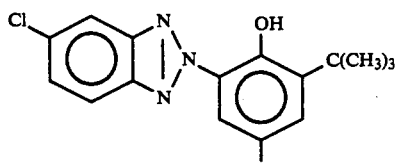
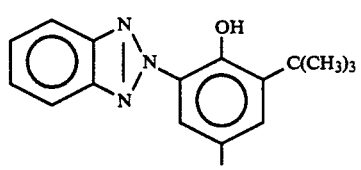
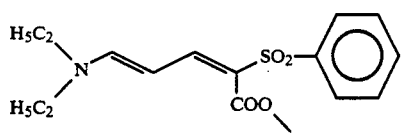
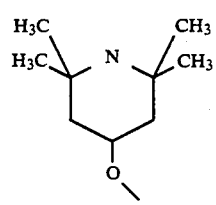
Specific examples of dyes of formula (Ia) of the present invention are described below, but the present invention is not to be construed as being limited to these compounds.
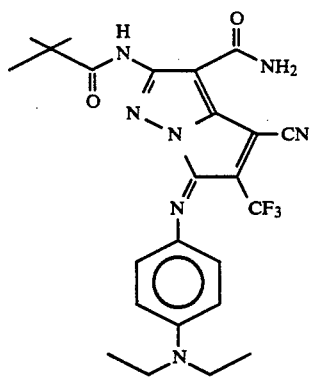
A-1
-continued
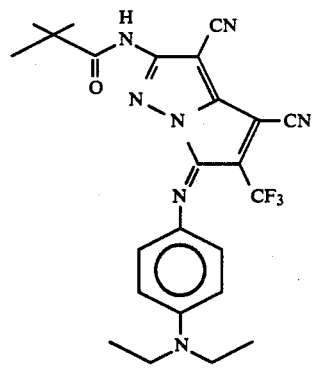
A-2
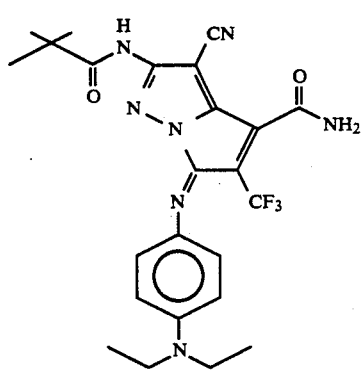
A-3
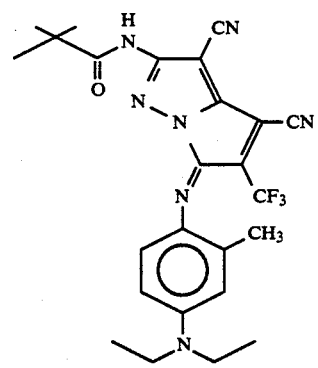
A-4
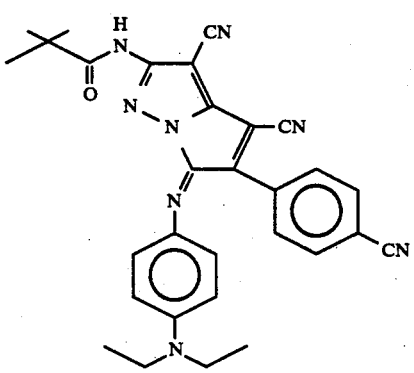
A-5

-continued
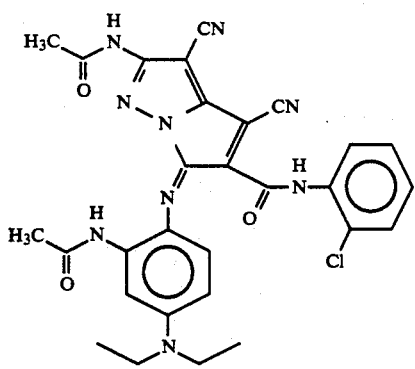
A-6
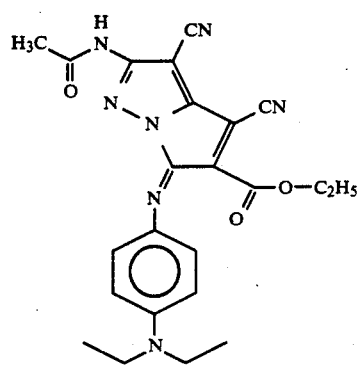
A-7
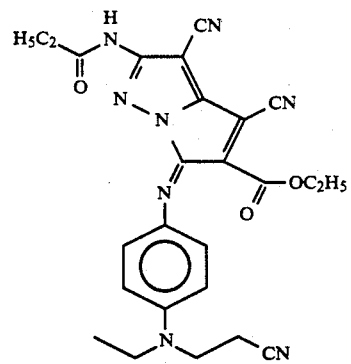
A-8
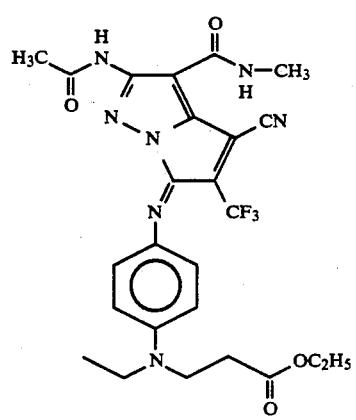
A-9
-continued
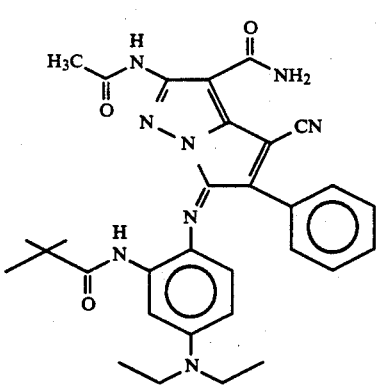
A-10
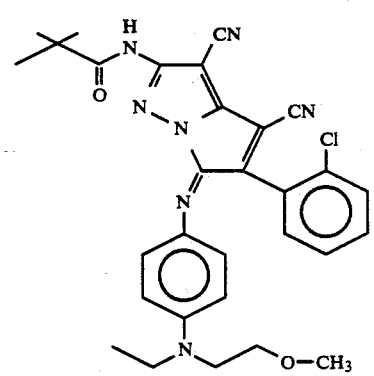
A-11
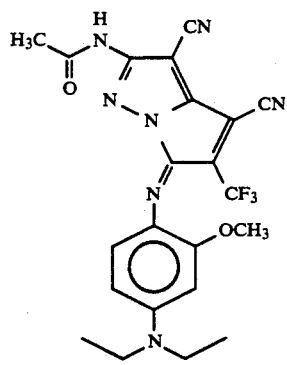
A-12
A-13

-continued
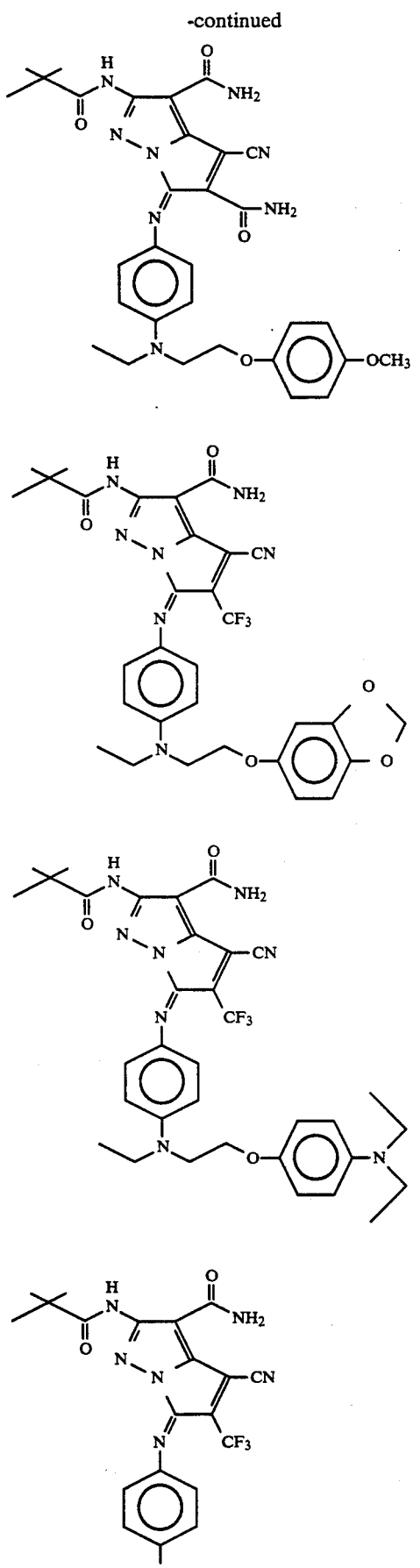
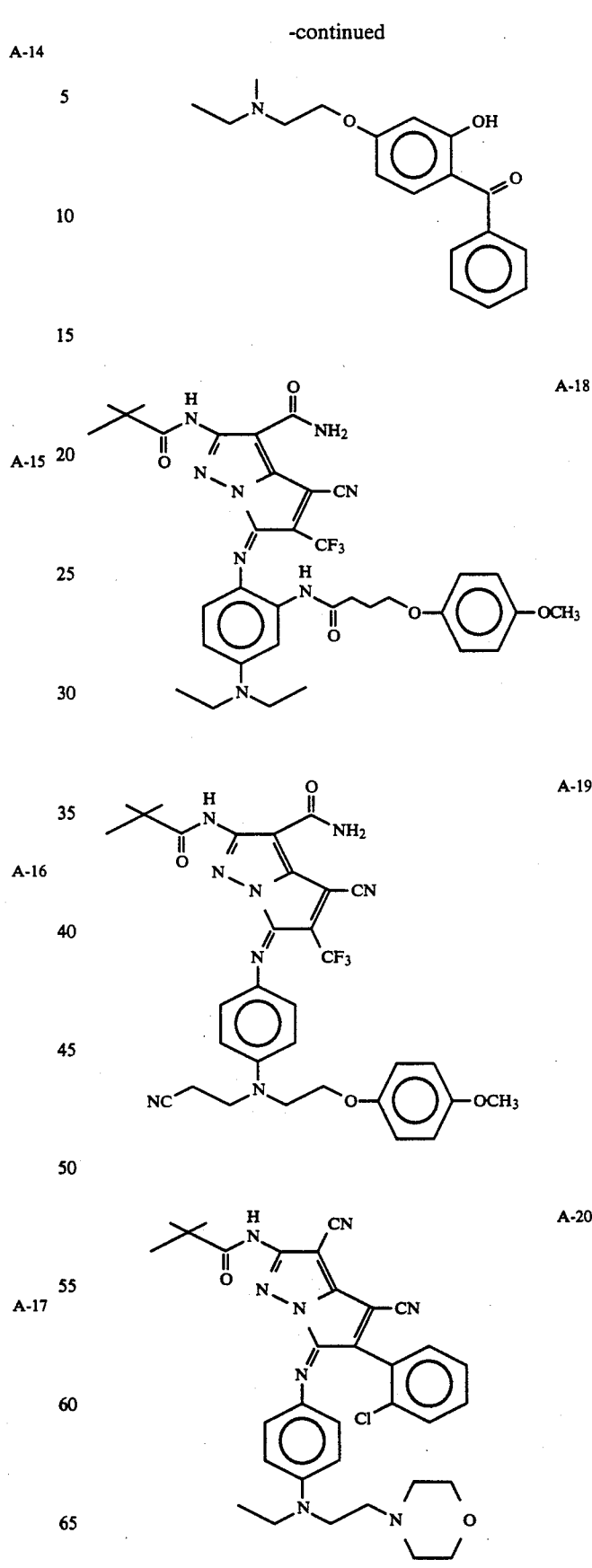

-continued
A-21
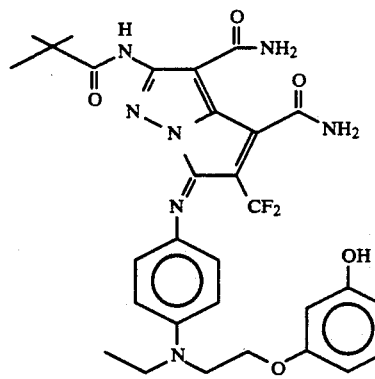
A-22
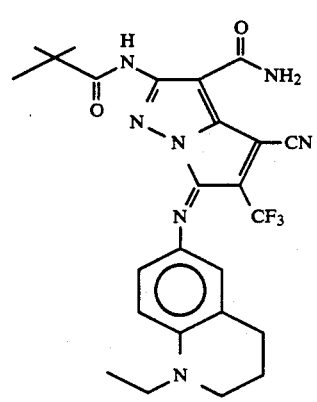
A-23
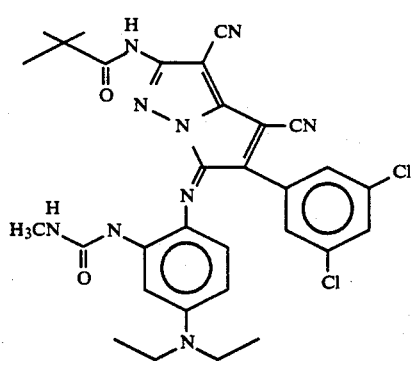
A-24
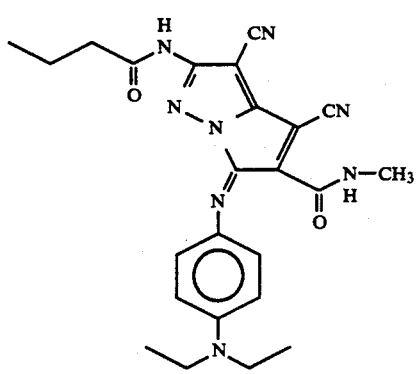
-continued
A-25
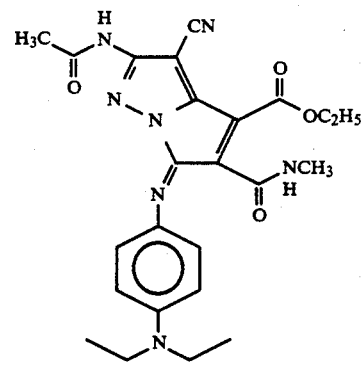
A-26
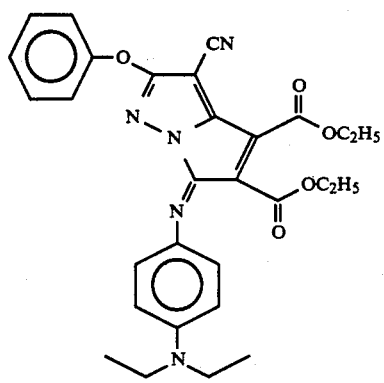
A-27
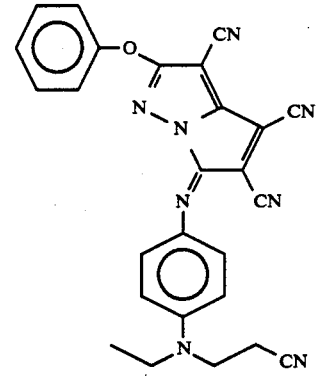
A-28
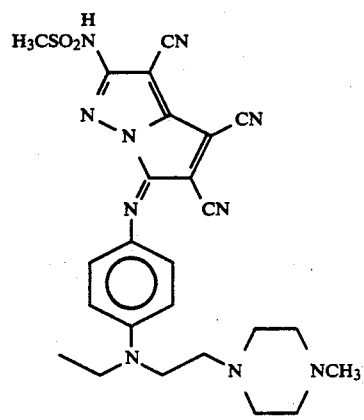

-continued

-continued
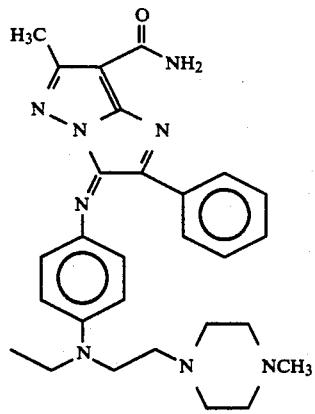
A-36
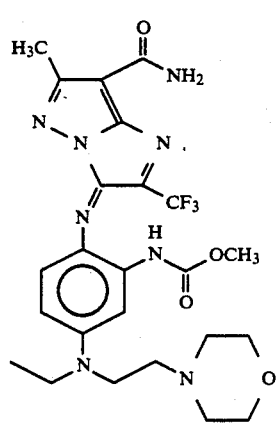
A-37
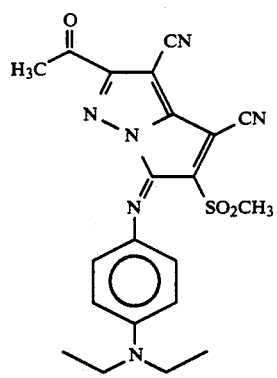
A-38
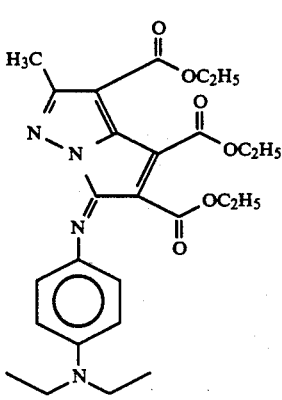
A-39
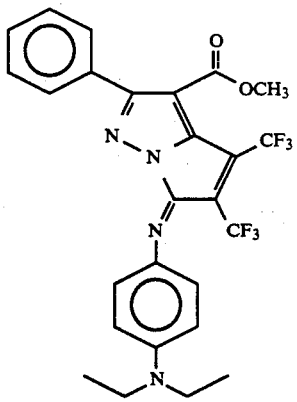
A-40
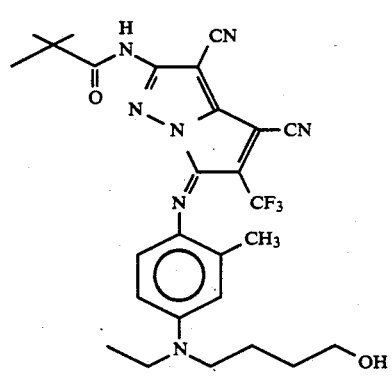
A-41
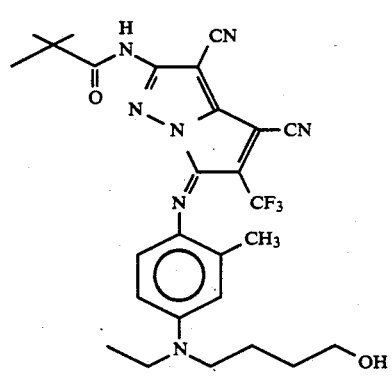
A-42
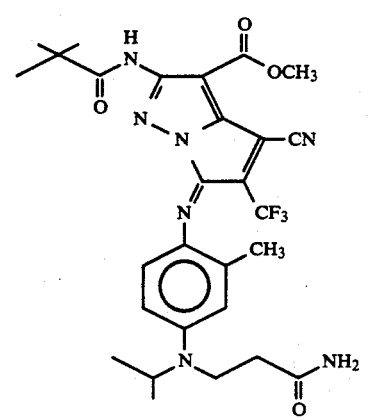
A-43

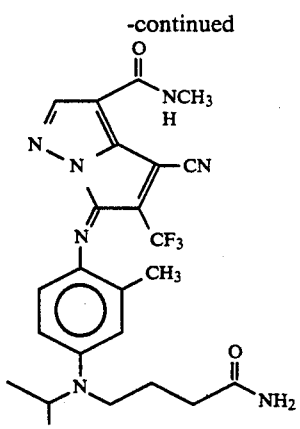

A-44

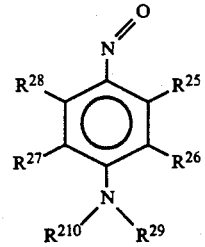
(C)

An example of the synthesis of dyes of formula (Ia) is described below.

SYNTHESIS EXAMPLE

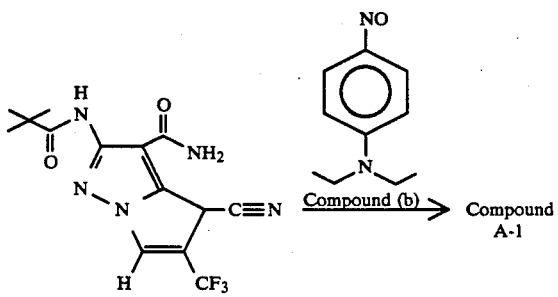

Compound (a)

1.0 g of Compound (a), 10 ml of ethanol and 0.60 g of Compound (b) were stirred, to which 0.32 g of acetic anhydride was added dropwise. After the addition, the mixture was stirred for 30 minutes and crystals precipitated were removed by filtration. The crystals were then washed with ethanol and dried to obtain 1.2 g of Compound A-1.

Yield: 88%
m.p.: Greater than 230° C.
λmax: 641 nm (in ethyl acetate)
εmax: $7.8 \times 10^4$ liter·mol$^{-1}$·cm$^{-1}$ The other dyes of the present invention can be produced by the same method as described above.

In the present invention, dyes of the formula (Ia) are used as cyan color-forming dyes. These may be used as a combination of two or more thereof, if desired.

If desired, one or more dyes of formula (Ia) of the present invention can be combined with any other conventional known dye(s).

Where the present invention is applied to an ink sheet which should have satisfactory storage stability, incorporation of a combination of dyes is preferred.

Use of the thermal transferring dyes of the present invention is described below.

The thermal transfer dye donating material of the present invention may be in any form of a sheet or a long roll or ribbon. The cyan dyes of the present invention and other yellow and magenta dyes which are combined therewith are generally positioned on a support in such a way that they separately form independent regions. For instance, an yellow dye region, a magenta dye region and a cyan dye region are positioned on a support either in planar order or in a linear order. Alternatively, an yellow dye, a magenta dye and a cyan dye may be provided separately on different supports to prepare three thermal transfer dye donating materials; and of the dyes may be transferred from them to a thermal transfer dye receiving material.

Dyes of formula (Ia) for use in the present invention are new, and methods of producing them are described below.

Dyes of formula (Ia) for use in the present invention can be produced by oxidative coupling of Coupler (A) and a Developing Agent (B). Production of Couplers (A) is disclosed in U.S. Pat. No. 4,728,598 and Japanese Patent Application No. 2-121670.

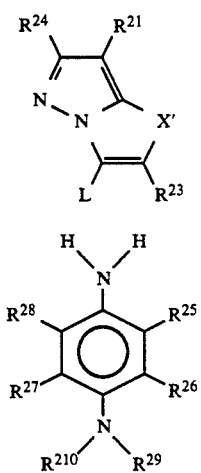

In formulae (A) and (B), L represents a hydrogen atom, or a group released from the formula during coupling reaction; X' represents

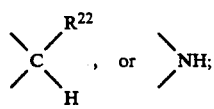

and $R^{21}$ to $R^{210}$ have the same meanings as in formula (Ia). Formula (A) may also exist in the form of its tautomer.

Alternatively, dyes of formula (Ia) may also be produced by reacting a Coupler (A) and a nitroso Compound (C) by dehydration condensation. In this case, L in formula (A) is a hydrogen atom.

The cyan dyes of the present invention and yellow and magenta dyes to be combined with them may be dissolved or dispersed in an appropriate solvent along with a binder resin and then coated on a support, or alternatively, the resulting solution or dispersion may be printed on a support, for example, by gravure printing. The thickness of the dye donating layer is generally from about 0.2 μm to about 5 μm, especially from about 0.4 μm to about 2 μm, as a dry thickness. The amount of the dyes incorporated in the dye donating layer is generally from 0.03 to 1.0 g/m$^2$, preferably from 0.1 to 0.6 g/m$^2$.

Suitable binder resins to be used along with the above-mentioned dyes include any known binder resins. In general, those which have a high heat-resistance and which do not interfere with transfer of dyes under heating are selected. For instance, examples of usable binder resins include polyamide resins, polyester resins, epoxy resins, polyurethane resins, polyacrylic resins (for example, polymethyl methacrylate, polyacrylamide, polystyrene-2-acrylonitrile), vinyl resins (for example, polyvinyl pyrrolidone), polyvinyl resins (for example, vinyl chloride-vinyl acetate copolymer), polycarbonate resins, polystyrenes, polyphenylene oxides, cellulose resins (for example, methyl cellulose, ethyl cellulose, carboxymethyl cellulose, cellulose acetate hydrogen phthalate, cellulose acetate, cellulose acetate propionate, cellulose acetate butyrate, cellulose triacetate), polyvinyl alcohol resins (for example, polyvinyl alcohol, and partially saponified polyvinyl alcohols such as polyvinyl acetal and polyvinyl butyral), petroleum resins, rosin derivatives, chromanindene resins, terpene resins, and polyolefin resins (for example, polyethylene, polypropylene).

The amount of the binder resin to be used in the present invention is preferably from about 80 to about 600 parts by weight, more preferably from 20 to 600 parts by weight, to 100 parts by weight of dye.

An ink solvent, which may be any known solvent, is used for dissolving or dispersing the above-described dyes and binder resins, in the present invention.

Suitable supports for the thermal transfer dye donating material of the present invention include any known supports. For instance, usable supports are polyethylene terephthalate, polyamides, polycarbonates, glassine paper, condenser paper, cellulose esters, fluorine polymers, polyethers, polyacetals, polyolefins, polyimides, polyphenylenesulfide, polypropylene, polysulfone, and cellophane.

The thickness of the support of the thermal transfer dye donating material of the present invention is generally from 2 to 30 μm.

For the purpose of preventing the thermal head from sticking to the surface of the dye donating material, a slipping layer may be provided. Such a slipping layer may be composed of a lubricating substance with or without a polymer binder, for example, a surfactant or a solid or liquid lubricant or a mixture thereof.

It is preferred that the dye donating material is subjected to an adhesion preventing treatment on the surface of the support not coated with the dye donating layer, to prevent the material from sticking to a thermal head due to the heat of the head during printing where a heated thermal head is applied to the material from the back surface thereof, and to improve the slidability of a thermal head on the surface of the material.

For instance, a heat-resistant slip layer of (1) a reaction product of a polyvinyl butyral resin and an isocyanate, (2) an alkali metal or alkaline earth metal salt of a phosphate and (3) a filler may be provided on the intended surface of the support for this purpose. Preferred examples of polyvinyl butyral resins are those having a molecular weight of from about 60,000 to 200,000 and a glass transition point of from 80° to 110° C. and as well as those containing having the vinyl butyral moiety in a proportion of from 15 to 40% by weight in view of the sufficient number of the reaction sites reactive with isocyanates. An example of an alkali metal or alkaline earth metal salts of phosphates which can be used is Gafac RD720 (product by Toho Chemical Co.). The amount of such a salt can be from 1 to 50% by weight, preferably from 10 to 40% by weight, to the polyvinyl butyral resin.

It is desired that the heat-resistant slip layer has a heat-resistant layer below this layer. For instance, such a heat-resistant layer may be composed of a combination of a thermosetting synthetic resin and a hardening agent for the resin, for example, a combination of a polyvinyl butyral and a polyisocyanate, a combination of an acryl-polyol and a polyisocyanate, a combination of a cellulose acetate and a titanium chelating agent and a combination of a polyester and an organic titanium compound.

The dye donating material of the present invention may have a hydrophilic barrier layer for the purpose of preventing diffusion of dyes in the direction of the support. Such a hydrophilic dye-barrier layer contains a hydrophilic substance useful for this purpose. In general, excellent results are obtained by using gelatin, poly(acrylamide), poly(isopropylacrylamide), butyl methacrylate-grafted gelatin, ethyl methacrylate-grafted gelatin, cellulose monoacetate, methyl cellulose, poly(vinyl alcohol), poly(ethyleneimine), poly(acrylic acid), mixture of poly(vinyl alcohol) and poly(vinyl acetate), mixture of poly(vinyl alcohol) and poly(acrylic acid), or mixture of cellulose monoacetate and poly(acrylic acid). Especially preferred is poly(acrylic acid), cellulose monoacetate or poly(vinyl alcohol).

The dye donating material of the present invention may include a subbing layer. Preferred examples of subbing layers are acrylonitrile/vinylidene chloride/acrylic acid copolymer (14/80/6, by weight), butyl acrylate/2-aminoethyl methacrylate/2-hydroxyethyl methacrylate copolymer (30/20/50, by weight), linear/saturated polyesters such as Bostic 7650 (product by M Heart Co. of Bostic Chemical), and chlorinated high-density poly(ethylenetrichloroethylene) resins. The amount of the subbing layer to be coated is not specifically limited but may be, in general, from 0.1 to 2.0 g/m$^2$.

The thermal transfer dye donating material of the present invention is attached to a thermal transfer image receiving material, and heat energy is applied to any of the materials of the assembly, preferably to the back surface of the thermal transfer dye donating material using a heating means, for example, with a thermal head or the like in accordance with any desired image information. As a result, the dye in the dye donating layer is transferred to the thermal transfer image receiving material in accordance with the degree of the heat energy imparted to the assembly. As a result, a color image having high sharpness and sufficient gradation with good resolution is formed on the image receiving material. The anti-fading agent to be in the thermal transfer dye donating material may also be transferred to the image receiving material in the same manner.

The heating means employed in image formation is not limited to just a thermal head but any other known means such as a laser (for example, a semiconductor laser), infrared flash, hot pen and other heating means may also be used.

In using a laser as the heat source, it is desired that the thermal transfer dye donating material contains a substance which strongly absorbs laser light. Where the thermal transfer dye donating material of the present invention is irradiated with laser light, the absorbing substance present in the material may convert the light energy to a heat energy and transmit the thus converted heat to the adjacent dye, whereby the dye is heated to a temperature suitable for transfer to a thermal transfer image receiving material.

Such an absorbing substance is in a layer provided below the dye in the material, and/or it may be blended with the dye in the material.

The details of this technique are disclosed in British Patent 2,083,726A.

Examples of lasers usable in the above-described process in the present invention are ion gas lasers such as argon or krypton ion gas lasers, metal vapor lasers such as copper, gold or cadmium vapor lasers, solid lasers such as ruby or YAG lasers, and semiconductor lasers such as gallium-arsenic lasers capable of radiating light in the infrared range of from 750 to 870 nm.

Semiconductor lasers are especially preferred because of their small size, low cost, stability, reliability, durability and ease of modulation.

Specific examples of suitable semiconductor lasers are Laser Model SDL-2420-H2 ® (manufactured by Spectrodiode Labs) and Laser Model SLD-304 V/W ® (manufactured by Sony).

The thermal transfer dye donating material of the present invention is combined with a thermal transfer image receiving material and can be used in various fields of printing and facsimile using various thermal printing systems, formation of image prints by magnetic recording systems, photomagnetic recording systems or optical recording systems, and formation of print images from television or a CRT image.

The details of such thermal transfer recording methods are set forth in JP-A-60-34895.

The thermal transfer image receiving material to be used in combination with the thermal transfer dye donating material of the present invention is one having an image receiving layer on a support. This is the layer receiving the dyes transferred from the thermal transfer dye donating material. The image receiving layer is preferably a layer which contains a substance capable of receiving the dyes transferred from the thermal transfer dye donating material during printing and of fixing the thus transferred dyes in the layer, alone or with any other binder substance, and the layer preferably has a thickness of approximately from 0.5 to 50 μm. Specific examples of substances which may be present in such an image receiving layer for receiving dyes transferred thereto from the thermal transfer dye donating material are polymers of the following resins.

(A) Resins having ester bonds

Polyester resins obtained by condensation of a dicarboxylic acid component such as terephthalic acid, isophthalic acid or succinic acid (the dicarboxylic acid component may have a sulfonic acid group, a carboxyl group or the like) and ethylene glycol, diethylene glycol, propylene glycol, neopentyl glycol, bisphenol A or the like; polyacrylate resins or polymethacrylate resins such as polymethyl methacrylate, polyvinyl methacrylate, polymethyl acrylate or polybutyl acrylate; polycarbonate resins; polyvinyl acetate resins; styrene-acrylate resins; and vinyltoluene-acrylate resins. Specific examples are described in JP-A-59-101395, JP-A-63-7971, JP-A-63-7972, JP-A-63-7973 and JP-A-60-294862. Vylon 290, Vylon 200, Vylon 280, Vylon 300, Vylon 103, Vylon GK-140 and Vylon GK-130 (all products by Toyobo Co., Ltd.) and ATR-2009 and ATR-2010 (both products by Kao Co.) are usable commercial products.

(B) Resins having urethane bonds

Polyurethane resins.

(C) Resins having amide bonds

Polyamide resins.

(D) Resins having urea bonds

Urea resins.

(E) Resins having sulfone bonds:

Polysulfone resins.

(F) Other resins having high polar bonds

Polycaprolactone resins, styrene-maleic anhydride resins, polyvinyl chloride resins, and polyacrylonitrile resins.

In addition to the above-described resins, mixtures of resins as well as copolymers of these resins may also be used.

The thermal transfer image receiving material may contain, especially in the image receiving layer, a high boiling point organic solvent or a thermal solvent as a substance accepting the dye transferred from the thermal transfer dye donating material of the present invention or as a promoter for diffusion of the dye.

Examples of suitable high boiling organic solvents and thermal solvents used for the purpose are the compounds described in JP-A-62-174754, JP-A-62-245253, JP-A-61-209444, JP-A-61-200538, JP-A-62-8145, JP-A-62-9348, JP-A-62-30247, and JP-A-62-136646.

The image receiving layer of the thermal transfer image receiving material may include a substance capable of accepting the transferred dye in the form of a dispersion dispersed in a water-soluble binder. Suitable water-soluble binders which can be used include various known water-soluble polymers. Preferred water-soluble polymers are those having groups capable of being crosslinked with a hardening agent.

The image receiving layer may comprise two or more layers, if desired. In the case, it is desired for the layer nearer to the support is made of a synthetic resin having a lower glass transition point or contains a high boiling point organic solvent or a thermal solvent for the purpose of enhancing the fixability of the transferred dye in the layer, while the outermost layer is made of a synthetic resin having a higher glass transition point and contains a minimum amount of a high boiling point organic solvent or a thermal solvent or contains neither a high boiling point organic solvent nor a thermal solvent for the purpose of preventing various difficulties or accidents due to adhesion of the surface, adhesion of the surface to other substances, re-transfer of the transferred dye to other substances, and blocking of the surface with the thermal transfer dye donating material attached thereto.

The total thickness of the image receiving layer is desirably within the range of from 0.5 to 50 μm, especially preferably from 3 to 30 μm. Where the image receiving layer is composed of two layers, the thickness of the outermost layer is preferably within the range of from 0.1 to 2 μm, especially preferably from 0.2 to 1 μm.

The thermal transfer image receiving material usable in the present invention may have an interlayer between the support and the image receiving layer.

Such an interlayer may be a cushion layer, a porous layer or a dye diffusion preventing layer, or a layer having two or more functions. It may also act as an adhesive layer.

The dye diffusion preventing layer is a layer having the function of preventing diffusion of the transferred dye to the support. The binder of the dye diffusion preventing layer may be either a water-soluble binder or an organic solvent-soluble binder. A water-soluble binder is preferred. Examples of the water-soluble binder for this layer are those described above as examples of the binder for the image receiving layer. Gelatin is especially preferred.

The porous layer is a layer having the function of preventing diffusion of the heat (imparted to the image receiving material during thermal transfer) from the image receiving layer to the support for the purpose of efficiently utilize the imparted heat.

The image receiving layer, cushion layer, porous layer, diffusion preventing layer and adhesive layer of the thermal transfer image receiving material for use in the present invention can contain a fine powder of silica, clay, talc, diatomaceous earth, calcium carbonate, calcium sulfate, barium sulfate, aluminium silicate, synthetic zeolite, zinc oxide, lithopone, titanium oxide, alumina or the like.

Suitable materials for the support of the thermal transfer image receiving material for use in the present invention include those which are durable and resistant to the transferring temperature and which satisfies all the necessary conditions of smoothness, whiteness, slidability, friction property, antistatic property and depression after transfer. For instance, paper supports such as synthetic paper (e.g., polyolefin synthetic paper, polystyrene synthetic paper), high-quality paper, art paper, coated paper, cast-coated paper, wall paper, lining paper, synthetic resin- or emulsion-impregnated paper, synthetic rubber latex-impregnated paper, synthetic resin-incorporated paper, sheet paper, cellulose fiber paper, polyolefin-coated paper (especially, paper as coated polyethylene on both surfaces thereof); various synthetic resin films or sheets of polyolefins, polyvinyl chloride, polyethylene terephthalate, polystyrene methacrylates or polycarbonates, as well as synthetic resin films or sheets surface-treated to impart a white reflectivity thereto; and laminates comprising any of these can be used.

The thermal transfer image receiving material for use in the present invention may contain a brightening agent. Examples of usable brightening agents are compounds described in K. Veenkataraman, *The Chemistry of Synthetic Dyes*, Vol. 5, Chap. 8, and JP-A-61-143752. More precisely, stilbene compounds, coumarin compounds, biphenyl compounds, benzoxazolyl compounds, naphthalimide compounds, pyrazoline compounds, carbostyryl compounds, and 2,5-dibenzoxazolethiophene compounds can be used.

The brightening agent may be incorporated into the material along with an anti-fading agent.

For the purpose of improving the releasability of the thermal transfer dye donating material of the present invention from the thermal transfer image receiving material after the thermal transfer process, a releasing agent is desirably incorporating into the layer of the dye donating material and/or the layer of the image receiving material, especially preferably into the outermost layers of the both materials facing each other.

Any known releasing agents, for example, solid or waxy substances such as polyethylene wax, amide wax or Teflon powder; fluorine surfactants or phosphate surfactants; as well as paraffin oils, silicone oils or fluorine oils can be used. Especially preferred are silicone oils.

Examples of silicone oils usable for this purpose include non-modified silicone oils as well as modified silicone oils such as carboxy-modified, amino-modified or epoxy-modified silicone oils. Specific examples of such silicone oils are various modified silicone oils as described in *Modified Silicone Oils* (issued by Shin-Etsu Silicone Co.), pages 6 to 18B. Where the oils are incorporated into an organic solvent binder, amino-modified silicone oils having groups capable of reacting with the crosslinking agent of the binder (for example, groups reacting with isocyanates) are effective. On the other hand, where they are emulsified and dispersed in a water-soluble binder, carboxy-modified silicone oils (for example, X-22-3710; trade name by Shin-Etsu Silicone Co.) are effective.

The layers of the thermal transfer dye donating material of the present invention as well as those of the thermal transfer image receiving material may be hardened with a hardening agent.

Where organic solvent-soluble polymers are hardened, the hardening agents as described in JP-A-61-199997 and JP-A-58-215398 may be used. Application of isocyanate hardening agents to polyester resins is especially preferred.

On the other hand, to harden water-soluble polymers, hardening agents as described in U.S. Pat. No. 4,678,739 (column 41), and JP-A-59-116655, JP-A-62-245261 and JP-A-61-18942 are suitable. More precisely, aldehyde hardening agents (e.g., formaldehyde), aziridine hardening agents, epoxy hardening agent

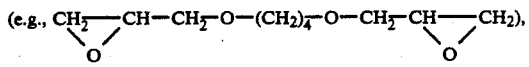

vinylsulfone hardening agents (e.g., N,N'-ethylene-bis(-vinylsulfonylacetamido)ethane), N-methylol hardening agents (e.g., dimethylol urea), as well as high polymer hardening agents (e.g., compounds described in JP-A-62-234157) can be used.

The thermal transfer dye donating material of the invention and the thermal transfer image receiving material may contain an anti-fading agent. The anti-fading agent may be, for example, an antioxidant, an ultraviolet absorbent as well as certain metal complexes.

Examples of antioxidants usable for this purpose are chroman compounds, coumaran compounds, phenol compounds (e.g., hindered phenols), hydroquinone derivatives, hindered amine derivatives, and spiroindane compounds. Additionally, the compounds described in JP-A-61-159644 can also be effectively used.

Examples of usable ultraviolet absorbents are benzotriazole compounds (such as those described in U.S. Pat. No. 3,533,794), 4-thiazolidone compounds (such as those described in U.S. Pat. No. 3,352,681), benzophenone compounds (such as those described in JP-A-56-2784), and other compounds as described in JP-A-54-48535, JP-A-62-136641 and JP-A-61-88256. Additionally, ultraviolet absorbing polymers described in JP-A-62-260152 are also effective.

Examples of usable metal complexes are the compounds as described in U.S. Pat. Nos. 4,241,155, 4,245,018 (columns 3 to 36) and 4,254,195 (columns 3 to 8), JP-A-62-174741 and JP-A-61-88256 (pages 27 to 29), and JP-A-1-75568 and JP-A-63-199248.

Specific examples of anti-fading agent usable in the present invention are described in JP-A-62-215272 (pages 125 to 137).

An anti-fading agent having the function of preventing the transferred dyes from fading may be previously added to the image receiving material or, alternatively, it may be supplied later to the material from an external source, for example, by transferring it from the dye donating material when attached to the image receiving material.

The above-described antioxidant, ultraviolet absorbent and metal complex can be used in combination, if desired.

The layers of the thermal transfer dye donating material of the present invention and those of the thermal transfer image receiving material may contain various surfactants as a coating aid as well as to improve the releasability, to improve the slide property, to prevent static charges and to accelerate developability.

Examples of surfactants usable for this purpose include nonionic surfactants, for example, saponins (steroid type), alkylene oxide derivatives (such as polyethylene glycol, polyethylene glycol alkyl ethers, polyethylene glycol alkylaryl ethers, polyethylene glycol esters, polyethylene glycol sorbitan esters, polyalkylene glycol alkylamines or amides, and silicone-polyethylene oxide adducts), glycidol derivatives (such as alkenylsuccinic acid polyglycerides, and alkylphenol polyglycerides), fatty acid esters of polyalcohols, and alkyl esters of saccharides; anionic surfactants containing an acid group such as a carboxyl group, a sulfo group, a phospho group, a sulfate ester group or a phosphate ester group, for example, alkylcarboxylic acid salts, alkylsulfonic acid salts, alkylnaphthalenesulfonic acid salts, alkylsulfates esters, alkylphosphate esters, N-acyl-N-alkyltaurins, sulfosuccinate esters, sulfoalkyl-polyethylene alkylphenyl ethers, and polyoxyethylene alkylphosphate esters; ampholytic surfactants such as amino acids, aminoalkylsulfonic acids, aminoalkylsulfates or phosphates, alkylbetains, and amine oxides; and cationic surfactants such as alkylamine salts, aliphatic or aromatic quaternary ammonium salts, heterocyclic quaternary ammonium salts such as pyridinium or imidazolium salts, and aliphatic or heterocyclic phosphonium or sulfonium salts. Specific examples of these surfactants are described, for example, in JP-A-62-173463 and JP-A-62-183457.

Where a substance accepting thermotransferring dyes, a releasing agent, an anti-fading agent, an ultraviolet absorbent, a brightening agent and other hydrophobic compounds are dispersed in a water-soluble binder, it is preferred to use a surfactant as a dispersion aid. The above-described surfactants as well as surfactants as described in JP-A-59-157636 (pages 37 to 38) are especially preferably employed for this purpose.

The layers of the thermal transfer dye donating material of the present invention and those of the thermal transfer image receiving material may contain organic fluoro-compounds to improve the slide property, to prevent static charges and to improve the releasability. Specific examples of organic fluoro-compounds usable for this purpose are fluorine surfactants such as those described in JP-B-57-9053 (columns 8 to 17), and JP-A-61-20944 and JP-A-62-135826; as well as hydrophobic fluorine compounds, for example, oily fluorine compounds such as fluorine oil and solid fluorine compounds such as tetrafluoroethylene resins.

The thermal transfer dye donating material of the present invention and the thermal transfer image receiving material may contain a mat agent. Examples of usable mat agents are those compounds described in JP-A-61-88256 (page 29) such as silicon dioxide, polyolefins or polymethacrylates, as well as the compounds described in JP-A-63-274944 and JP-A-63-274952 such as benzoguanamine resin beads, polycarbonate resin beads and AS resin beads.

The present invention is explained in more detail by way of the following examples, which, however, are not intended to restrict the scope of the present invention. Unless otherwise indicated, all parts, percents, ratios and the like are by weight.

EXAMPLE 1

Production of Dye Compound (1)

Dye Compound (1) was produced in accordance with the following production scheme:

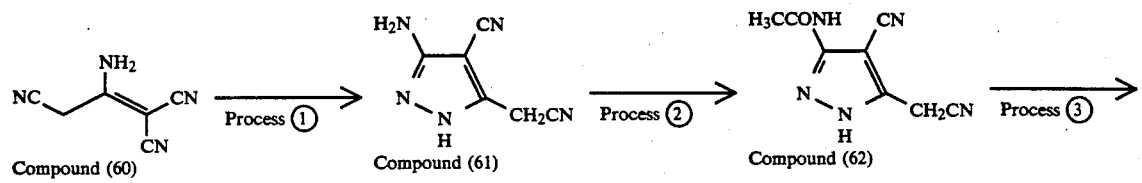

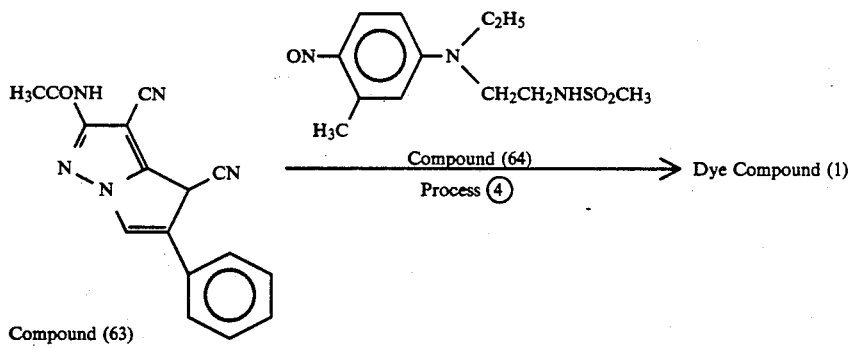

Compound (63)

Step ①: Production of Compound (61)

132 g of 2-amino-1,1,3-tricyano-1-propene (Compound (60)) was dispersed in one liter of ethanol, and 55ml of an aqueous 50% hydrazine solution was dropwise added thereto with cooling with ice over a period of 30 minutes. After the addition, the mixture was heated under reflux for 30 minutes and then cooled with ice, and the crystals precipitated were removed by filtration to obtain 103 g of Compound (61). Yield: 70%.

Step ②: Production of Compound (62)

16.0 g of Compound (61) was dissolved in 100 ml of acetonitrile, and 9.6 ml of pyridine was added thereto, and 10.3 g of acetyl chloride was dropwise added thereto at room temperature. The crystals precipitated were removed by filtration to obtain 114.6 g of an intermediate product (Compound (62)). Yield: 70%.

Step ③: Production of Compound (63)

2.4 g of the thus obtained Compound (62) and 2.6 ml of a 28% sodium methylate/methanol solution were dissolved in 20 ml of ethanol, and 2.6 g of phenacyl bromide was added thereto at room temperature. After Compound (62) was confirmed not present, 2.6 ml of a 28% sodium methylate/methanol solution was further added to the reaction system. After further reaction, ethyl acetate was added to the system, which was then neutralized with an aqueous hydrochloric acid solution. The ethyl acetate layer was dried with magnesium sulfate and ethyl acetate was removed therefrom by distillation under reduced pressure. The residue was purified by column chromatography to obtain 1.8 g of an intermediate product (Compound (63)). Yield: 48%.

Step ④: Production of Dye Compound (1)

50 mg of the thus obtained Compound (63) and 50 mg of Compound (64) were dissolved in ethanol, and one drop of acetic anhydride was added thereto. The crystals precipitated were removed by filtration to obtain 83.0 mg of the intended Dye Compound (1). Yield: 88.2%. This compound had a decomposition point of 270° C. or higher.

EXAMPLE 2

Production of Dye Compound (2)

Dye Compound (2) was produced in accordance with the following production scheme:

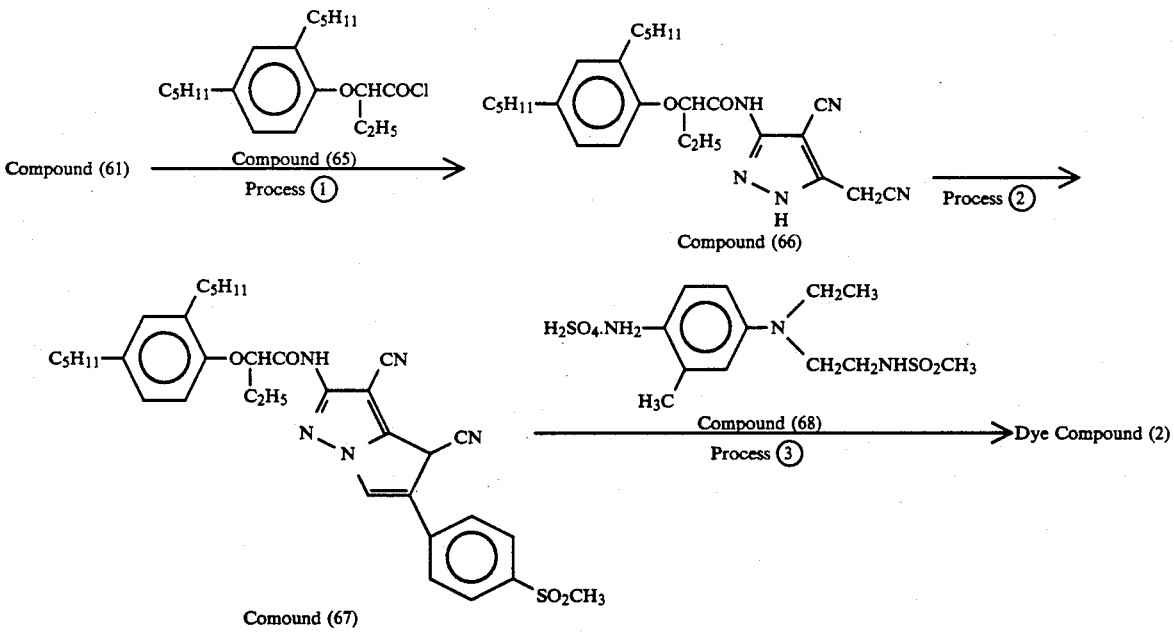

Step ①: Production of Compound (66)

30.0 g of Compound (61) and 57 ml of triethylamine were dissolved in 300 ml of acetonitrile, and 69.0 g of Compound (65) was added thereto and heated under reflux. After reaction for 2 hours, ethyl acetate was added to the reaction mixture, which was washed with water. The ethyl acetate layer was dried and ethyl acetate was removed therefrom by distillation under reduced pressure. 200 ml of a mixed solvent of ethyl acetate/hexane (1/1 by vol) was added to the residue for recrystallization, and the crystals precipitated were removed by filtration to obtain 73.6 g of an intermediate product (Compound (66)). Yield: 80.0%.

Step ②: Production of Compound (67)

(66) and 3.5 ml of a 28% sodium methylate/methanol solution were dissolved in 42 ml of acetonitrile, and 5.0 g of p-methanesulfonylphenacyl bromide was added thereto at room temperature. Next, 0.5 ml of triethylamine was added thereto and stirred for one hour. After reaction, ethyl acetate was added to the reaction mixture, which was washed with water. The ethyl acetate layer was dried and purified by column chromatography using alumina as a carrier to obtain 1.8 g of an intermediate product (Compound (67)). Yield: 18.9%.

Step ③: Production of Dye Compound (2)

581 mg of the thus obtained Compound (67) was dissolved in 10 ml of ethanol, and 625 mg of sodium carbonate as dissolved in 5 ml of water was added thereto. Further, 640 mg of Compound (68) and 670 mg of ammonium persulfate were added thereto and stirred for 30 minutes at room temperature. The crystals precipitated were thoroughly washed with water and removed by filtration to obtain 735 mg of the intended Dye Compound (2). Yield: 92.0%. This compound had a decomposition point of 250° C.

EXAMPLE 3

Production of Dye Compound (5)

Dye Compound (5) was produced in accordance with the following production scheme:

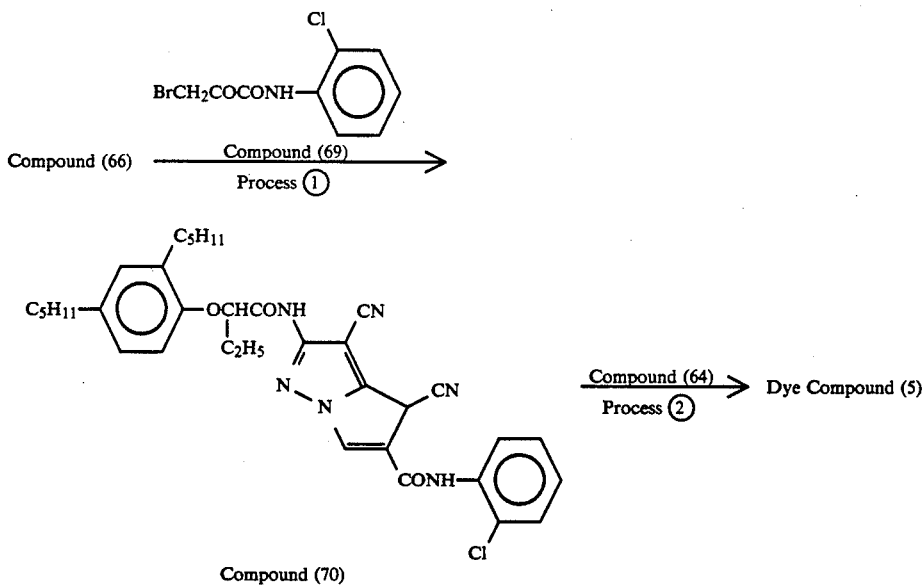

phy to obtain 1.2 g of an intermediate product (Compound (70)). Yield: 8.5%.

Step ②: Production of Dye Compound (5)

86 mg of the thus obtained Compound (70) was reacted with 35 mg of Compound (64) in the same manner as in step ④ in Example 1 to obtain 102 mg of the intended Dye Compound (5). Yield: 85.7%. This compound had a decomposition point of 220° C.

EXAMPLE 4

Production of Dye Compound (10)

In the same manner as in Example 3, Dye Compound (10) was produced in accordance with the following production scheme:

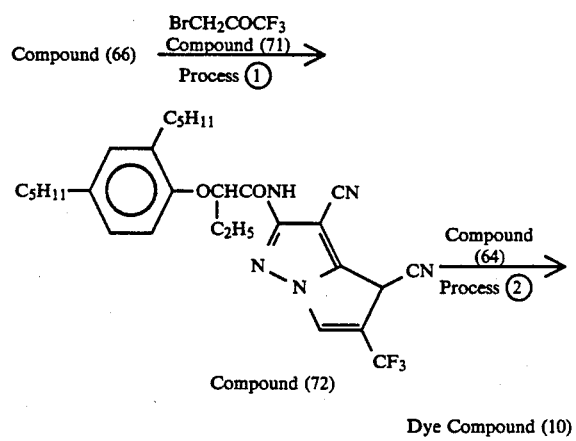

①: Formation of Compound (70) 10.2 g of Compound (66) and a 28% sodium methylate/methanol solution were dissolved in 100 ml of acetonitrile, and 6.3 g of Compound (69) as dissolved in 30 ml of methylene chloride was dropwise added thereto under reflux. After reaction, 200 ml of ethyl acetate was added to the reaction mixture, which was then washed with water. The ethyl acetate layer was dried and ethyl acetate was removed therefrom by distillation under reduced pressure. The residue was purified by column chromatogra- Step ①: Production of Compound (72)

4.5 g of Compound (66), 1.9 ml of a 28% sodium methylate/methanol solution and 1.9 g of Compound (71) were reacted in acetonitrile in the same manner as in step ① in Example 3 to obtain 1.4 g of an intermediate product (Compound (72)). Yield: 25.0%.

Step ②: Production of Dye Compound (10)

70 mg of the thus obtained Compound (72) was reacted with 35 mg of Compound (64) in the same manner as in step ④ in Example 1 to obtain 94 mg of the intended Dye Compound (10). Yield: 92.9%. This compound had a decomposition point of 270° C.

EXAMPLE 5

Production of Dye Compound (20)

Dye Compound (20) was produced in accordance with the following production scheme:

Step ①: Production of Compound (74)

14.0 g of Compound (73) was dispersed in 10 ml of ethanol, and 5.0 ml of an aqueous 50% hydrazine

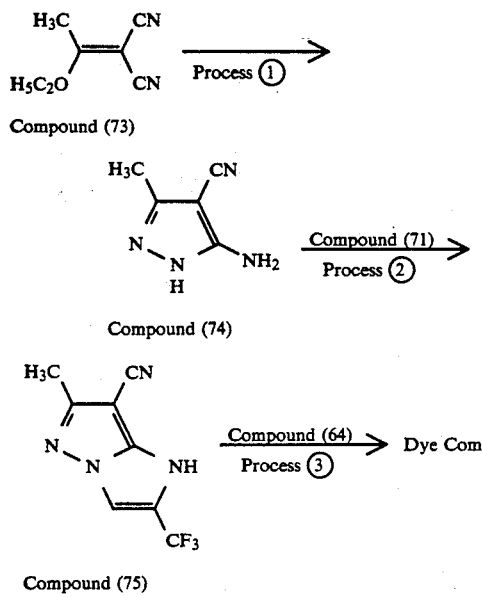

Compound (73)

Compound (74)

Compound (75)

solution was dropwise added thereto at room temperature. After reaction, ethanol was removed from the reaction mixture by distillation under reduced pressure, and a mixed solvent of ethyl acetate/hexane (1/1 by vol) was added to the residue for recrystallization. The crystal precipitated were removed by filtration to obtain 10.0 g of Compound (74). Yield: 78.7%.

Step ②: Production of Compound (75)

5.0 g of the thus obtained Compound (74), 7.7 ml of a 28% sodium methylate/methanol solution and 9.2 g of Compound (71) were heated in acetonitrile under reflux for 2 hours. After reaction, ethyl acetate was added to the reaction mixture for extraction, the ethyl acetate layer was removed by distillation under reduced pressure and the residue was stirred for 30 minutes in an oil bath having a temperature of from 120° C. to 130° C. After reaction, the residue was purified by column chromatography to obtain 2.3 g of an intermediate product (Compound (75)). Yield: 26.9%.

Step ③: Production of Dye Compound (20)

67 mg of the thus obtained Compound (75) was reacted with 78 mg of Compound (64) in the same manner as in step ④ of Example 1 to obtain 121 mg of the intended Dye Compound (20). Yield: 87.1%. This compound had a decomposition point of 190° C.

The identification of the compounds obtained above was carried out by means of a mass spectrum and a NMR spectrum.

EXPERIMENTAL EXAMPLE 1

FIG. 1 shows the absorption spectrum of Dye Compound (10) of the present invention obtained in the previous example, in ethyl acetate as a solvent in a visible light range. The absorption peak wavelength was 637.2 mm.

For comparison, the absorption spectrum of the following comparative Compound (A) is also shown in FIG. 1. It had an absorption peak wavelength of 644.3 nm.

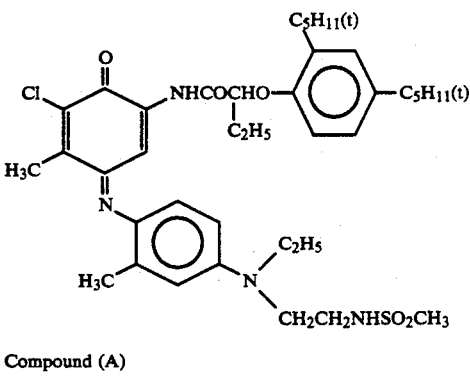

Compound (A)

Table 1 below shows the peak absorption wavelength of each of typical dye compounds of the present invention in ethyl acetate; and Table 2 below shows the molecular extinction coefficient thereof.

TABLE 1

| Dye Compound | Peak Absorption Wavelength (nm) |
| --- | --- |
| 1 | 594.6 |
| 2 | 611.7 |
| 3 | 618.4 |
| 4 | 635.5 |
| 5 | 679.0 |
| 6 | 635.8 |
| 7 | 647.9 |
| 8 | 659.4 |
| 9 | 633.9 |
| 10 | 637.2 |
| 11 | 602.0 |
| 12 | 637.1 |
| 13 | 618.0 |
| 14 | 622.9 |
| 15 | 656.8 |
| 16 | 603.1 |
| 19 | 633.2 |
| 20 | 617.0 |
| 21 | 618.1 |
| 22 | 579.6 |
| 29 | 591.3 |

TABLE 2

| Dye Compound | Molecular Extinction Coefficient ε (liter · mol$^{-1}$ · cm$^{-1}$) |
| --- | --- |
| 1 | 3.78 × 10$^4$ |
| 10 | 6.98 × 10$^4$ |
| 20 | 7.73 × 10$^4$ |
| 29 | 3.06 × 10$^4$ |

As is obvious from the data shown above, the dyes of the present invention had little side absorption in the blue range and the main absorption of each of these dyes showed good toe sharpness in a short wavelength range. The dyes had a much higher molecular extinction coefficient than conventional phenol cyan dyes. Such a higher molecular extinction coefficient means that the amount of the dye, when used for forming a cyan image, may be smaller to achieve the desired color density. The fact that the side absorption of the dye in the blue range is slight and that the toe sharpness of the main absorption of the dye in a short wavelength range is good means is quite advantageous for color reproduction.

In addition, the dyes of the present invention have good fastness to heat, light and wet heat.

EXPERIMENTAL EXAMPLE 2

A coating liquid comprising 43 parts (by weight as solid content—the same hereunder) of fine hollow grains of a styrene-acrylate copolymer (having grain size of 0.3 to 0.4 μm), 17 parts of gaseous phase anhydrous silica (having grain size of 12 nm), 12 parts of styrene-butadiene copolymer latex, 18 parts of polyvinyl acetate latex and 10 parts of fine grains of polymethyl methacrylate (having grain size of 8 μm) was coated on commercial non-coated base paper (weight: 64 g/m$^2$), using a wire bar coater to prepare an ink jet recording paper. The coated amount was 10 g/m$^2$ on a solids basis.

The recording paper was recorded with an ink liquid (A) comprising the components described below by ink jet recording, using an electrostatic acceleration type ink jet device equipped with a head having a nozzle orifice diameter of 50 μm. The number of dots was 8 dots/mm.

| Ink Liquid (A): | |
| --- | --- |
| Dye (18) of Invention | 6 g |
| Diethyl Phthalate | 30 g |
| Diisopropyl Adipate | 44 g |
| N,N-diethyldodecanamide | 20 g |

The ink liquid had a specific resistance of $3.6 \times 10^7$ ω.cm (at 25° C.) and a viscosity of 7.1 cp (at 25° C.). The jettability of the ink liquid from the nozzle was good, and a sharp cyan image having a high density was formed.

The thus formed image was exposed to room light for 3 months, whereupon the decrease in the image density was found to be not more than 1%.

Additionally, the present invention is explained further by way of the following examples illustrating manufacture of thermal transfer dye donating material samples, thermal transfer image receiving material samples, printing using both materials and testing of the transferred samples. However, these examples are not intended to restrict the scope of the present invention.

EXAMPLE 6

Formation of Thermal Transfer Dye Donating Material Sample (1-1):

A 6 μm-thick polyethylene terephthalate film (product of Teijin Co.), the back surface of which had been surface-treated to be heat-resistant and lubricative, was used as a support. The following composition for forming a thermal transfer dye donating layer was coated on the opposite surface of the film using wire bar-coating in a dry thickness of 1.5 μm. Accordingly, a thermal transfer dye donating material Sample (1-1) was prepared.

| Composition for Forming Thermal Transfer Dye Donating Layer: | |
| --- | --- |
| Dye (A-1) | 10 mmol |
| Polyvinyl Butyral Resin | 3 g |

| -continued | |
| --- | --- |
| Composition for Forming Thermal Transfer Dye Donating Layer: | |
| (Denka Butyral 5000-A, product by Denki Kagaku Kogyo K.K.) | |
| Toluene | 40 ml |
| Methyl Ethyl Ketone | 40 ml |
| Polyisocyanate (Takenate D110N, product by Takeda Chemical Industries Co., Ltd.) | 0.2 ml |

Other thermal transfer dye donating material Samples (1-2) to (1-9) of the present invention and a comparative Sample (1-10) were prepared in the same manner as above, except that Dye (A-1) was replaced by the dye indicated in Table 3 below.

Formation of Thermal Transfer Image Receiving Material Sample:

A 150 μm-thick synthetic paper (YUPO-FPG-150, product of Oji Petrochemical Co.) was used as a support. The following composition for forming a thermal transfer image receiving layer was coated on one surface of the support using wire bar-coating in a dry thickness of 8 μm. Accordingly, a thermal transfer image receiving material sample (1) was prepared. Drying of the coated layer was effected first with a drier for pre-drying and then in an oven having a temperature of 100° C. for 30 minutes.

| Composition for Forming Thermal Transfer Image Receiving Layer: | |
| --- | --- |
| Polyester Resin (Vylon-200, product by Toyobo Co., Ltd.) | 22 g |
| Polyisocyanate (KP-90, product by Dainippon Ink & Chemicals, Inc.) | 4 g |
| Amino-Modified Silicone Oil (KF-857, product by Shin-Etsu Silicone Co.) | 0.5 g |
| Methyl Ethyl Ketone | 85 ml |
| Toluene | 85 ml |
| Cyclohexanone | 15 ml |

Each thermal transfer dye donating material Samples (1-1) to (1-10) prepared as above and the thermal transfer image receiving material sample prepared as above were attached to each other, with the dye donating layer facing to the image receiving layer, and a thermal head was applied to the side of the support of the dye donating material for printing. The printing conditions were an output power of the thermal head of 0.25 W/dot, a pulse width of from 0.15 to 15 msec, and a dot density of 6 dots/mm. Accordingly, a cyan color image was printed on the image receiving layer of the image receiving material. The cyan color image thus formed was sharp.

The thus printed material was stored under the conditions of exposure to light from a fluorescent lamp of 17,000 luxes for 14 days, whereupon the stability of the printed color image was tested. The status-A reflection density of the irradiation-tested sample was measured at the area having a status-A reflection density of 1.0 before irradiation. The percentage of the former density (after irradiation) to the reflection density of 1.0 before the test was obtained, which demonstrates the stability (light-fastness) of each sample. The results obtained are shown in Table 3 below.

TABLE 3

| No. | Dye | Maximum Density | Light Fastness (%) | Remarks |
|---|---|---|---|---|
| 1-1 | A-1 | 1.8 | 90 | Invention |
| 1-2 | A-2 | 1.7 | 91 | Invention |
| 1-3 | A-3 | 1.8 | 90 | Invention |
| 1-4 | A-4 | 1.9 | 91 | Invention |
| 1-5 | A-10 | 1.8 | 90 | Invention |
| 1-6 | A-14 | 1.7 | 92 | Invention |
| 1-7 | A-15 | 1.7 | 92 | Invention |
| 1-8 | A-19 | 1.6 | 93 | Invention |
| 1-9 | A-31 | 1.7 | 87 | Invention |
| 1-10 | a | 2.1 | 84 | Comparison |

Comparative Dye (a):

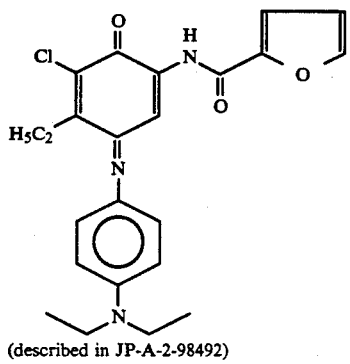

(described in JP-A-2-98492)

From the results in Table 3 above, it is obvious that the dyes of formula (Ia) of the present invention had a higher light-fastness than the comparative Dye (a).

EXAMPLE 7

FIG. 2 shows the absorption spectrum of Dye (A-1) of the present invention in ethyl acetate as the solvent and that of Comparative Dye (a) in the same solvent.

In FIG. 2, the solid line shows the absorption spectrum of Dye (A-1) and the dotted line that of Comparative Dye (a).

The peak absorption wavelength and the extinction coefficient at the peak absorption wavelength of these dyes are described below.

Dye (A-1)

$\lambda$max: 641 nm
$\epsilon$max: $7.8 \times 10^4$ liter.mol$^{-1}$.cm$^{-1}$ Comparative Dye (a)

$\lambda$max: 637 nm
$\epsilon$max: $3.0 \times 10^4$ liter.mol$^{-1}$.cm$^{-1}$ As is noted from FIG. 2, Dye (A-1) of the present invention had a more sharp absorption than comparative Dye (a) and the former had less yellow side-absorption than the latter.

In addition, it is obvious that Dye (A-1) of the present invention has a much higher $\epsilon$max value than the comparative Dye (a).

EXAMPLE 8

Thermal transfer dye donating material samples (3-1), (3-2) and (3-3) were prepared in the same manner as in Example 6, except that the resin and dye as shown in Table 4 below were used in place of the polyvinyl butyral resin and Dye (A-1).

Using these samples, printing was achieved in the same way as in Example 6 on the same image receiving material as that used in Example 6. As a result, a sharp image with no blur was formed in every sample, as shown in Table 4 below. All the images formed had good fastness to light.

TABLE 4

| Dye Donating Material Sample | Resin | Dye | Maximum Density | Light Fastness (%) |
|---|---|---|---|---|
| 3-1 | Ethyl Cellulose | A-1 | 1.8 | 90 |
| 3-2 | Cellulose Acetate Butyrate | A-2 | 1.7 | 91 |
| 3-3 | Polysulfone | A-4 | 1.9 | 91 |

The following examples illustrate combinations comprising other thermal transfer image receiving material samples described below and the above-described thermal transfer dye donating material sample of the present invention.

EXAMPLE 9

Formation of Thermal Transfer Image Receiving Material

A 150 $\mu$m-thick synthetic paper (YUPO-FPG-150, product by Oji Petrochemical Co.) was used as a support. The following composition for forming a thermal transfer image receiving layer was coated on one surface of the support using wire bar-coating in a dry thickness of 10 $\mu$m. Accordingly, a thermal transfer image receiving material sample was prepared. Drying of the coated layer was effected first with a drier for pre-drying and then in an oven having a temperature of 100° C. for 30 minutes.

| Composition for Forming Thermal Transfer Image Receiving Layer: | |
|---|---|
| Polyester Resin No. 1 (1*) | 2.0 g |
| Amino-Modified Silicone Oil (KF-857, product by Shin-Etsu Silicone Co.) | 0.5 g |
| Epoxy-Modified Silicone Oil (KF-100T, product by Shin-Etsu Silicone Co.) | 0.5 g |
| Methyl Ethyl Ketone | 85 ml |
| Toluene | 85 ml |
| Cyclohexanone | 30 ml |

(*1) Polyester Resin No. 1

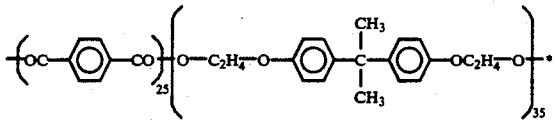

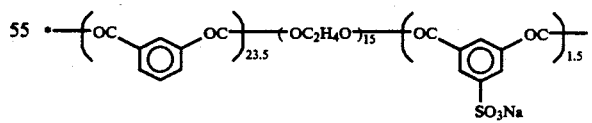

The image receiving material sample thus prepared was combined with one of the thermal transfer dye donating material samples of the present invention as prepared in Example 6 and printing was effected in the same way as in Example 6. As a result, sharp images were formed in all the printed samples. Additionally, the light-fastness of all the printed samples was found excellent.

EXAMPLE 10

Formation of Thermal Transfer Image Receiving Material Sample

A resin-coated paper was prepared by laminating a 15 μ-thick polyethylene and a 25 μ-thick polyethylene on both surfaces of a 200 μ-thick paper. The following composition for forming an image receiving layer was coated on the surface of the 15 μ-thick polyethylene laminate using wire bar-coating in a dry thickness of 10 μm. After drying, a thermal transfer image receiving material sample was prepared.

| Composition for Forming Image Receiving Layer: | |
|---|---|
| Polyester Resin No. 1 | 25 g |
| Amino-Modified Silicone Oil (KF 857, product by Shin-Etsu Silicone Co.) | 0.8 g |
| Polyisocyanate (KP-90, product by Dainippon Ink & Chemicals, Inc.) | 4 g |
| Methyl Ethyl Ketone | 100 ml |
| Toluene | 100 ml |

Using the sample thus prepared, printing was effected in the same way as in Example 6. As a result, sharp images were formed in all the printed samples. Additionally, the light-fastness of all the printed samples was excellent.

EXAMPLE 11

Formation of Thermal Transfer Image Receiving Material Sample

An organic solvent solution of a dye accepting polymer having the composition (B') described below was dispersed in an aqueous gelatin solution having the composition (A') described below by emulsification with a homogenizer to prepare a gelatin dispersion of the dye accepting substance.

| (A') Aqueous Gelatin Solution: | |
|---|---|
| Gelatin | 2.3 g |
| Sodium Dodecylbenzenesulfonate (5% aqueous solution) | 20 ml |
| Water | 80 ml |
| (B') Dye Accepting Polymer Solution: | |
| Polyester Resin (Vylon 300, product by Toyobo Co., Ltd.) | 7.0 g |
| Carboxy-Modified Silicone Oil (X-22-3710, product by Shin-Etsu Silicone Co.) | 0.7 g |
| Methyl Ethyl Ketone | 20 ml |
| Toluene | 10 ml |
| Triphenyl Phosphate | 1.5 g |

A solution prepared by dissolving 0.5 g of a fluorine surfactant (a) $C_3F_7SO_2N(C_3H_7)CH_2COOK$ in 10 ml of a mixed solvent of water/methanol (1/1 by vol) was added to the resulting dispersion, to prepare a composition for coating an image receiving layer. The thus prepared composition was coated on a 150 μm-thick synthetic paper (YUPO-SGG-150, product by Oji Petrochemical Co.), one surface of which had been surface-treated by a corona-discharge, using wire bar-coating in a wet thickness of 75 μm. The coated layer was then dried.

Using the thermal transfer dye donating material samples of the present invention as prepared in Example 6 and the thermal transfer image receiving material sample prepared above, printing was effected in the same way as in Example 6.

The obtained images had a high color density and were sharp, and the fastness thereof was excellent.

EXAMPLE 12

Formation of Thermal Transfer Image Receiving Material Sample

Using the image receiving layer coating composition described below, a thermal transfer image receiving material sample was prepared in the same manner as in Example 6.

Composition for Forming Image Receiving Layer

The same image receiving layer coating composition used in Example 6 was used, except that 7 g of the following ultraviolet absorbent was added.

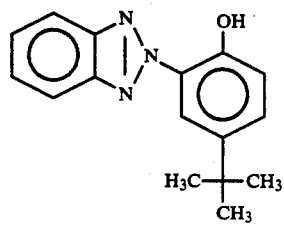

The thus prepared thermal transfer image receiving material sample was combined with one of the thermal transfer dye donating materials of the present invention as prepared in Example 6, and printing was effected in the same manner as in Example 6. As a result, all the printed images had a high density and were sharp. In addition, the light-fastness of the images were higher than that of the images obtained in Example 6.

As is obvious from the above-described data, a sharp and fast color image having a high density can be transferred to an image receiving material from the thermal transfer dye donating material of the present invention.

While the invention has been described in detail and with reference to specific embodiments thereof, it will be apparent to one skilled in the art that various changes and modifications can be made therein without departing from the spirit and scope thereof.

What is claimed is:

1. A dye compound of general formula (I):

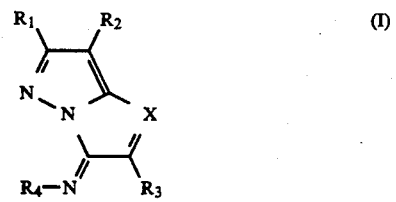

wherein
$R_1$ is selected from a group consisting of a hydrogen atom, a halogen atom, an aliphatic group, an aromatic group, a heterocyclic group, an alkoxy group, an aryloxy group, an alkenyloxy group, an amino group, an aliphatic, aromatic or heterocyclic acyl group, an aliphatic or aromatic oxycarbonyl group, an aliphatic or aromatic acyloxy group, an aliphatic or aromatic oxysulfonyl group, an aliphatic or aromatic sulfonyloxy group, an acylamino group, a carbamoyl group, a sulfonamido group, a sulfamoyl group, a sulfamido group, an imido group, a ureido group, an aliphatic, aromatic or heterocyclic sulfonyl group, an aliphatic or aromatic thio group, a hydroxyl group, a cyano group, a carboxyl group or a salt thereof, a nitro group and a sulfonic acid group or a salt thereof;

$R_2$ and $R_3$ each is a substituent having a Hammett's substituent constant $\sigma_p$ of 0.10 or more;

X represents a nitrogen atom or

$R_5$ represents a substituent having a Hammett's substituent constant $\sigma_p$ of at least 0.35; and $R_4$ represent an aromatic group of an unsaturated heterocyclic group bonded to the nitrogen atom in the formula via an unsaturated carbon atom.

2. The dye compound as claimed in claim 1, wherein $R_2$ and $R_3$ each is selected from the group consisting of a substituted alkyl group, a cyano group, an aliphatic, aromatic or heterocyclic acyl group, a carboxyl group or a salt thereof, a substituted or unsubstituted carbamoyl group, an alkoxycarbonyl group, a substituted aromatic group, a heterocyclic group, a nitro group, an azo group, a substituted amino group, a substituted alkoxy group, an alkylsulfonyloxy group, an acyloxy group, an arylsulfonyloxy group, a phosphoryl group, a sulfamoyl group, an aliphatic, aromatic or heterocyclic sulfonyl group, and a sulfonic acid group or a salt thereof.

3. The dye compound as claimed in claim 1, wherein $R_2$, $R_3$, and $R_5$ each is a substituent having a Hammett's substituent constant $\sigma_p$ of 0.35 or more.

4. The dye compound as claimed in claim 3, wherein $R_2$, $R_3$, and $R_5$ each is selected from the group consisting of a substituted alkyl group, a cyano group, an aliphatic, aromatic or heterocyclic acyl group, a carboxyl group or a salt thereof, a carbamoyl group, an alkoxycarbonyl group, a substituted aromatic group, a heterocyclic group, a nitro group, an azo group, a substituted amino group, a substituted alkoxy group, an alkylsulfonyloxy group, a phosphoryl group, a sulfamoyl group, an aliphatic, aromatic or heterocyclic sulfonyl group, and a sulfonic acid group or a salt thereof.

5. The dye compound as claimed in claim 1, wherein $R_5$ is a substituent having a Hammett's substituent constant $\sigma_p$ of 0.60 or more.

6. The dye compound as claimed in claim 5, wherein $R_5$ is selected from the group consisting of a cyano group, a nitro group, and an aliphatic, aromatic or heterocyclic sulfonyl group.

7. The dye compound as claimed in claim 1, group wherein $R_2$ is a $CO_2R_{31}$ group wherein $R_{31}$ represents an alkyl group having 1 to 8 carbon atoms or a $CONHR_{32}$ wherein $R_{32}$ represents an alkyl group having 1 to 8 carbon atoms or an aryl group having 6 to 18 carbon atoms, $R_3=CF_3$ and $R_5=CN$.

8. The dye compound as claimed in claim 1, wherein $R_2=CN$, $R_3=CF_3$ or $C_3F_7$, and $R_5=CN$.

* * * * *